United States Patent
Wakamiya et al.

(10) Patent No.: US 11,066,431 B2
(45) Date of Patent: Jul. 20, 2021

(54) COMPLEX AND METHOD FOR PRODUCING SAME

(71) Applicant: KYOTO UNIVERSITY, Kyoto (JP)

(72) Inventors: Atsushi Wakamiya, Kyoto (JP); Masashi Ozaki, Kyoto (JP); Yasujiro Murata, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 16/481,463

(22) PCT Filed: Jan. 26, 2018

(86) PCT No.: PCT/JP2018/002571
§ 371 (c)(1),
(2) Date: Jul. 29, 2019

(87) PCT Pub. No.: WO2018/139607
PCT Pub. Date: Aug. 2, 2018

(65) Prior Publication Data
US 2019/0345176 A1   Nov. 14, 2019

(30) Foreign Application Priority Data

Jan. 27, 2017   (JP) .............................. JP2017-013651

(51) Int. Cl.
| | | |
|---|---|---|
| *C07F 7/22* | (2006.01) | |
| *H01G 9/20* | (2006.01) | |
| *H01L 51/00* | (2006.01) | |
| *H01L 51/42* | (2006.01) | |

(52) U.S. Cl.
CPC ......... *C07F 7/2204* (2013.01); *H01G 9/2059* (2013.01); *H01L 51/0077* (2013.01); *H01L 51/424* (2013.01)

(58) Field of Classification Search
None
See application file for complete search history.

(56) References Cited

U.S. PATENT DOCUMENTS

2013/0320836 A1* 12/2013 Kanatzidis ........... C09K 11/666
                                                                313/483

OTHER PUBLICATIONS

Gurnani et al. Dalton Transactions, 2013, 42, 8364.*
Ogami, Yuhei et al., Near IR sensitive Sn based perovskite solar cells with high current density reaching 30mA/cm2, 2016 IEEE Explore 43rd Photovoltaic Specialists Conference, Nov. 2016, pp. 0808-0811, IEEE, New York, NY, US.
Yang, W.S. et al., High-performance photovoltaic perovskite layers fabricated through ntramolecular exchange, Science Express, May 21, 2015, pp. 1-8, AAAS, New York, NY, US.
Hao, Feng et al., Solvent-Mediated Crystallization of CH3NH3SnI3 Films for Heterojunction Depleted Perovskite Solar Cells, 2015, J. Am. Chem. Soc., 132: 11445-11452, Am. Chem. Soc., Washington, DC, US.
Dennington, A.J. et al., Synthesis and structure of pseudo-three dimensional hybrid iodobismuthate semiconductors, Nov. 28, 2016, Dalton Transaction, 45, 17974-17979, Royal Society of Chemistry, London, UK.
Ozaki M. et al., Solvent-Coordinated Tin Halide Complexes as Purified Precursors for Tin-Based Perovskites, Oct. 20, 2017, ACS Omega, 2: 7016-7021, Am. Chem. Soc., Washington, DC, US.
Kojima A. et al., Organometal Halide Perovskites as Visible-Light Sensitizers for Photovoltaic Cells, Apr. 14, 2009, J. Am. Chem. Soc., 131(17): 6050-6051, Washington, DC, US.
Lee, M. et al., Efficient Hybrid Solar Cells Based on Meso-Superstructured Organometal Halide Perovskites, Sep. 2, 2012, Science, 338: 643-647, AAAS, New York, NY, US.
WIPO, Intern'l Prelim. Report on Patentability, dated Jul. 2019, WIPO, Geneva, Switzerland.

* cited by examiner

*Primary Examiner* — Clinton A Brooks
(74) *Attorney, Agent, or Firm* — Liang Legal Group, PLLC

(57) ABSTRACT

A complex has a structure of formula (1A): $SnX_n \cdot (m)L$, wherein X is at least one type of halogen atoms, L is a polar solvent molecule, n is a value from 1.5 to 2.5, and m is a value from 0.3 to 1.9. A perovskite compound has a structure of formula (2A): $RSnX_j$, wherein Sn has an oxidation number from 1.5 to 2.5, R is at least one type of a monovalent cation, X is at least one type of halogen atoms, and j is a value from 2.5 to 3.5, and the perovskite compound is free of tin oxide; or a perovskite compound has a structure of formula (2B): $R_2M^2BiX_i$, wherein R is at least one type of a monovalent cation, X is at least one type of halogen atoms; $M^2$ is a monovalent metal, and i is a value from 5.0 to 7.0.

6 Claims, 24 Drawing Sheets

COMPLEX AND METHOD FOR PRODUCING SAME

TECHNICAL FIELD

The present invention relates to a complex, and a manufacturing method of the same.

BACKGROUND ART

In recent years, solar power generation has attracted public attention as a clean energy, accompanied by advancement in development of solar cells. A solar cell using a perovskite compound for its light absorbing layer has rapidly been brought into focus as a next generation solar cell, manufacturable at low cost. For example, Non-Patent Literature 1 reports a solution-type solar cell, using a perovskite compound for its light absorbing layer. Non-Patent Literature 2 reports that a solid-type perovskite solar cell can demonstrate high efficiency.

As the perovskite compound used for the perovskite solar cell, lead-containing perovskite compound such as $CH_3NH_3PbI_3$ are widely used. However, with recent needs for environment-friendly perovskite solar cell to be developed, there are requests for development of lead-free perovskite compound, as a perovskite compound applicable to the light absorbing layer of solar cell.

$CH_3NH_3SnI_3$, having tin in place of lead, is a possible lead-free perovskite compound applicable to the light absorbing layer of solar cell. Tin ion ($Sn^{2+}$) is, however, labile unlike lead ion ($Pb^{2+}$), and is easily oxidized to produce $Sn^{4+}$. The tin-containing perovskite compound is partially oxidized to demonstrate metal characteristics, rather than semiconductor characteristics. Hence at present, the solar cell that employs the tin-containing perovskite compound lacks reproducibility, and a good solar cell has not been obtained yet. It is even difficult to evaluate performances inherent to the tin-containing perovskite compound, and this interferes with the development of perovskite compounds suitable for perovskite solar cells.

CITATION LIST

Non-Patent Literature

Non-Patent Literature 1: Journal of the American Chemical Society, 2009, 131, 6050-6051.
Non-Patent Literature 2: Science, 2012, 388, 643-647.

SUMMARY OF THE INVENTION

Technical Problem $SnI_2$ employable as a starting material for tin-containing perovskite compounds is commercially available, but only with a considerably low purity. For example, some of $SnI_2$ reagents even marketed with an indication of 99.9% grade contain approximately 10% by mass of $SnI_4$. In order to have highly stable lead-free perovskite compounds to be applied to solar cells, it is indispensable to develop a halogenated tin compound with a high purity. The same issue can apply to manufacture of a perovskite compound having bismuth ion ($Bi^{3+}$) and monovalent metal ion ($M^+$) instead of lead ion ($Pb^{2+}$).

From this point of view, it is therefore an object of the present invention to provide a complex that contains a high concentration of tin ion ($Sn^{2+}$) or bismuth ion ($Bi^{3+}$) and is suitable for manufacturing a lead-free perovskite compound.

Solution to the Problem

In consideration of the aforementioned problems, the present inventors found from our thorough investigations that a complex having a compound having a predetermined chemical composition and polar solvent molecule, contains a high concentration of tin ion ($Sn^{2+}$) or bismuth ion ($Bi^{3+}$), and is suitable for manufacturing a lead-free perovskite compound. The present inventors went through further investigations on the basis of such findings, and arrived at the present invention. More specifically, the present invention encompasses the following embodiments:

Item 1. A complex represented by general formula (1A):

$$SnX_n \cdot (m)L$$

where, X represents at least one type of halogen atom; L represents a polar solvent molecule; n represents a value of 1.5 to 2.5; and m represents a value of 0.3 to 2.8.

Item 2. The complex according to item 1, wherein L represents N,N-dimethylformamide or dimethylsulfoxide.

Item 3. The complex according to item 1 or 2, wherein X represents an iodine atom or bromine atom.

Item 4. The complex according to any one of items 1 to 3, being a needle crystal.

Item 5. The complex according to any one of items 1 to 4, being a perovskite precursor.

Item 6. A manufacturing method for a complex represented by the general formula (1):

$$M^1 X_k \cdot (m)L$$

where, $M^1$ represents Sn or Bi; X represents at least one type of halogen atom; L represents a polar solvent molecule; k represents a value of 1.5 to 3.5; and m represents a value of 0.3 to 2.8, the manufacturing method comprising:
adding a poor solubility solvent dropwise to a polar solvent solution of a compound represented by general formula (3):

$$M^1 X_k$$

where, $M^1$, X and k are the same as those described above.

Item 7. The manufacturing method according to item 6, further comprising removing by filtration an insoluble matter from the polar solvent solution, prior to adding the poor solubility solvent dropwise.

Item 8. A perovskite compound, which is free of contamination with tin oxide, represented by general formula (2A):

$$RSnX_j$$

where, Sn has an oxidation number of 1.5 to 2.5; R represents at least one type of monovalent cation; X represents at least one type of halogen atom; and j represents a value of 2.5 to 3.5.

Item 9. A perovskite compound represented by general formula (2B):

$$R_2 M^2 BiX_i$$

where, R represents at least one type of monovalent cation; X represents at least one type of halogen atom; $M^2$ represents a monovalent metal; and i represents a value of 5.0 to 7.0.

Item 10. The perovskite compound according to item 8 or 9, wherein R represents at least one type of cation selected from the group consisting of an alkali metal cation, a monovalent transition metal cation, a cation represented by $R^1NH_3^+$ ($R^1$ represents a monovalent substituted or unsubstituted hydrocarbon group), and a cation represented by formula:

[Chemical Formula 1]

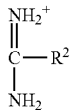

wherein $R^2$ represents a hydrogen atom or a monovalent substituted or unsubstituted hydrocarbon group.

Item 11. A manufacturing method of a perovskite compound represented by general formula (2A):

$RSnX_j$ where, R represents at least one type of monovalent cation; X represents at least one type of halogen atom; and j represents a value of 2.5 to 3.5, or represented by general formula (2B):

$R_2M^2BiX_i$ where, R and X are the same as those described above; $M^2$ represents a monovalent metal; and i represents a value of 5.0 to 7.0, wherein the manufacturing method comprises the step of allowing:

the complex obtained by the manufacturing method described in item 6 or 7 to react with;

a compound represented by general formula (4):

RX where, R and X are the same as those described above; and a compound represented, as needed, by general formula (5):

$M^2X$ where, $M^2$ and X are the same as those described above.

Item 12. The manufacturing method according to item 11, wherein R represents at least one type of cation selected from the group consisting of an alkali metal cation, a monovalent transition metal cation, a cation represented by $R^1NH_3^+$ ($R^1$ represents a monovalent substituted or unsubstituted hydrocarbon group), and a cation represented by formula:

[Chemical Formula 2]

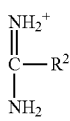

($R^2$ represents a hydrogen atom or monovalent substituted or unsubstituted hydrocarbon group).

Item 13. The manufacturing method according to item 11 or 12, wherein the reaction is carried out in a polar solvent.

Item 14. The manufacturing method according to item 13, further including: removing by filtration an insoluble matter from a solution of the polar solvent, prior to the reaction.

Item 15. The manufacturing method according to any one of items 11 to 14, wherein the reaction is carried out under heating.

Item 16. A perovskite solar cell using the complex described in any one of items 1 to 5, or the perovskite compound described in any one of items 8 to 10.

Advantageous Effects of Invention

The complexes in the present invention contain a high purity of tin ion ($Sn^{2+}$) or bismuth ion ($Bi^{3+}$). Hence, the complexes of the present invention are suitable for manufacturing lead-free perovskite compounds.

DETAILED DESCRIPTION

Figure 1:
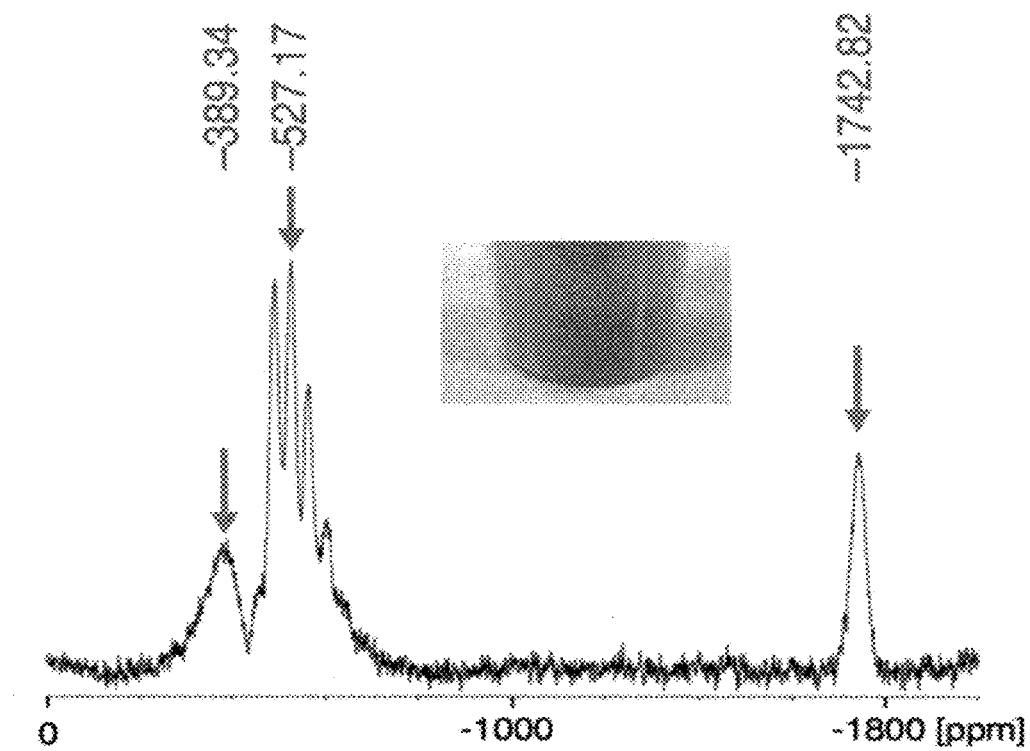
FIG. 1 is a $^{119}$Sn MAS NMR spectrogram of $SnI_2$ used as a starting material in Reference Example 1.

In this specification, "monovalent hydrocarbon group" is exemplified by alkyl group, aryl group or aralkyl group.

The "alkyl" group in this specification is preferably straight-chain, branched or cyclic alkyl group having 1 to 20 carbon atoms. Specific examples of the alkyl group include methyl group, ethyl group, n-propyl group, 2-propyl group, n-butyl group, 1-methylpropyl group, 2-methylpropyl group, tert-butyl group, n-pentyl group, 1-methylbutyl group, 1-ethylpropyl group, tert-pentyl group, 2-methylbutyl group, 3-methylbutyl group, 2,2-dimethylpropyl group, n-hexyl group, 1-methylpentyl group, 1-ethylbutyl group, 2-methylpentyl group, 3-methylpentyl group, 4-methylpentyl group, 2-methylpentan-3-yl group, 3,3-dimethylbutyl group, 2,2-dimethylbutyl group, 1,1-dimethylbutyl group, 1,2-dimethylbutyl group, 1,3-dimethylbutyl group, 2,3-dimethylbutyl group, 1-ethylbutyl group, 2-ethylbutyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, n-nonadecyl group, n-icosyl group, cyclopropyl group, cyclobutyl group, cyclopentyl group, and cyclohexyl group.

The "aryl" group in this specification is preferably aryl group having 6 to 20 carbon atoms. Specific examples of the aryl group include phenyl group, indenyl group, pentalenyl group, naphthyl group, azulenyl group, foluorenyl group, phenanthrenyl group, anthracenyl group, acenaphthylenyl group, biphenylenyl group, naphthacenyl group, and pyrenyl group.

The "aralkyl group" in this specification is preferably aralkyl group having 7 to 20 carbon atom. Specific examples of the aralkyl group include benzyl group, phenethyl group, 1-phenylpropyl group, 2-phenylpropyl group, 3-phenylpropyl group, 1-phenylbutyl group, 2-phenylbutyl group, 3-phenylbutyl group, 4-phenylbutyl group, 1-phenylpentylbutyl group, 2-phenylpentylbutyl group, 3-phenylpentylbutyl group, 4-phenylpentylbutyl group, 5-phenylpentylbutyl group, 1-phenylhexylbutyl group, 2-phenylhexylbutyl group, 3-phenylhexylbutyl group, 4-phenylhexylbutyl group, 5-phenylhexylbutyl group, 6-phenylhexylbutyl group, 1-phenylheptyl group, 1-phenyloctyl group, 1-phenylnonyl group, 1-phenyldecyl group, 1-phenylundecyl group, 1-phenyldodecyl group, 1-phenyltridecyl group, and 1-phenyltetradecyl group.

In this specification, the "alkyl group", "aryl group" and "aralkyl group" may have substituent(s). The "substituent" is exemplified by the aforementioned monovalent hydrocarbon groups, halogen atom, —OR$^{1a}$ (R$^{1a}$ represents a hydrogen atom or the aforementioned monovalent hydrocarbon group), —SR$^{1b}$ (R$^{1b}$ represents a hydrogen atom or the aforementioned monovalent hydrocarbon group), nitro group, amino group, cyano group, sulfo group, carboxy group, carbamoyl group, aminosulfonyl group, and oxo group. The number of substituent(s), when contained, is not specifically limited, and is preferably 10 or smaller, more preferably 5 or smaller, and even more preferably 3 or smaller.

In this specification, the "halogen atom" is exemplified by fluorine atom, chlorine atom, bromine atom and iodine atom.

1. Complex

The complex in the present invention is represented by general formula (1A):

where, X represents at least one type of halogen atom. L represents a polar solvent molecule. n represents a value of 1.5 to 2.5. m represents a value of 0.3 to 2.8.

With such structure, the complex in the present invention is a complex containing a high purity of tin ion (Sn$^{2+}$), since tin ion (Sn$^{2+}$) stays highly stable, and is less likely to be oxidized. Hence, even when dissolved into a polar solvent in order to manufacture a perovskite compound, the complex may be dissolved within a time distinctively shortened from the case where a commercially available SnI$_2$ is used, and also may improve the productivity. When the perovskite compound is manufactured using the complex in the present invention, the obtainable solar cell will have well-reproduced performance by virtue of good stability of tin ion (Sn$^{2+}$), and will have good solar cell performances. It is also expectable to open the way to develop the perovskite compound suitable for perovskite solar cell, since performances inherent to the tin-containing perovskite compound may be evaluated.

In general formula (1A), Sn means a Sn cation that occupies the B-site, when the perovskite compound is obtained by using the complex in the present invention as a starting material.

In general formula (1A), the halogen atom represented by X is preferably fluorine atom, chlorine atom, iodine atom, or bromine atom, from the viewpoint that a perovskite compound thus manufactured will have a light absorption range in longer wavelength regions, will have higher short circuit current density, and will more easily be improved in power conversion efficiency (PCE) and internal quantum efficiency (IQE). Each X more preferably represents iodine atom or bromine atom. It is even more preferable that all Xs are iodine atoms. Only a single type, or two or more types, of the halogen atom may be used. Bromine atom is preferable, from the viewpoint of expanding the band gap of the obtainable perovskite compound, and of making electrons and holes more easily extractable from a perovskite layer (light absorbing layer).

In general formula (1A), the polar solvent molecule represented by L is not specifically limited, and is preferably any of those having a structure of ketone, ester, ether or the like, and a boiling point of around 35 to 250° C. Specific examples include N,N-dimethylformamide (DMF), dimethylsulfoxide (DMSO), sulfolane, N-methypyrrolidone, propylene carbonate, α-acetyl-γ-butyrolactone, tetramethylene sulfoxide, ethylcyano acetate, acetylacetone, 3-methoxy-N,N-dimethylpropaneamide, N,N'-dimethylethyleneurea, 1,1,3,3-tetramethylurea, 2-acetylcyclohexanone, 1,3-dimethyl-3,4,5,6-tetrahydro-2(1H)-pyrimidinone, 3,4-dihydro-1(2H)-naphthalenone, cyclopentanone, cyclohexanone, cycloheptanone, aniline, piperidine, pyridine, 4-tert-butylpyridine, 4-amylpyridine, 4-aminopyridine, 2-amylpyridine, 4-methylpyridine, pentafluoropyridine, 2,4,6-tetramethylpyridine, 2,6-di-tert-butyl-4-methylpyridine, 4-pyridineethylamine, cyclooctanone, 2,5-dimethoxytetrahydrofurane, 1,4,7,10-tetraoxacyclododecane, ethyl p-toluate, 1,2-dimethoxybenzene, tetrahydrofurfuryl acetate, cyclohexyl acetate, cyclopentyl methyl ether, phenylethylamine, ethylenediamine, triethylamine, diisopropylethylamine, and hydrazine. Among them, preferable are N,N-dimethylformamide (DMF) or dimethylsulfoxide (DMSO), in view of their ability to form coordination bond centered round a metal.

In general formula (1A), n represents a value of 1.5 to 2.5, which is more preferably 1.8 to 2.2, from the viewpoint of making the perovskite material more easily manufacturable, and more easily be improved in power conversion efficiency (PCE) and internal quantum efficiency (IQE).

In general formula (1A), m represents a value of 0.3 to 2.8, which is more preferably 0.5 to 2.5, from the viewpoint of making the perovskite material more easily manufacturable, and more easily be improved in power conversion efficiency (PCE) and internal quantum efficiency (IQE). Note in a case where X represents an iodine atom and L represents DMSO, m preferably represents a value of 0.3 to 1.9, which is more preferably 0.5 to 1.5.

As the complex that satisfies these conditions and is represented by general formula (1A), preferably used are $SnI_2 \cdot DMF$, $3SnI_2 \cdot 2DMF$ ($SnI_2 \cdot (2/3)DMF$), $SnI_2 \cdot DMSO$, $SnBr_2 \cdot 2DMSO$, $SnBr_2 \cdot DMF$, and $SnF_2 DMSO$.

The complex in the present invention, satisfying the aforementioned conditions, is likely to be obtained in the form of needle microcrystal. The complex in the present invention, when formed as a film on a substrate, orients horizontally to the substrate, and is capable of yielding a nearly flat film. Note that "nearly flat film" in the present invention means that the film, when measured under a scanning electron microscope, has a difference in height of 50 nm or smaller within a 500 nm×500 nm area in the horizontal direction. Now the flatness of a film composed of the complex in the present invention is defined on the basis of a freely selected point of measurement set as a reference point, with a difference from the thickest part of the film within a measured area assumed as an upper limit value, and with a difference from the thinnest part assumed as a lower limit value, when measured on a cross section of the film composed of the complex in the present invention, under a scanning electron microscope (cross sectional SEM).

The complex in the present invention, satisfying the aforementioned conditions, can yield the perovskite compound as a result of release of the polar solvent molecule having been coordinated, and concurrent reaction with a desired compound (halogenated tin, for example), as described later. That is, the complex in the present invention can be used as a perovskite precursor. These complexes may be used as a precursor of a high-element-purity perovskite material as will be explained in Examples, and their tin ion (Sn') will not easily be oxidized, so that use of the complexes in the present invention can yield a lead-free perovskite compound with higher purity and higher stability, and use of the complex can also yield a perovskite solar cell with high reproducibility and advanced performances.

2. Manufacturing Methods for the Complexes

A manufacturing method of a complex according to the present invention is a manufacturing method of a complex represented by general formula (1):

$M^1 X_k \cdot (m) L$ where, $M^1$ represents Sn or Bi; X represents at least one type of halogen atom; L represents a polar solvent molecule; k represents a value of 1.5 to 3.5; and m represents a value of 0.3 to 2.8, wherein the manufacturing method includes:
adding poor solubility solvent dropwise to a polar solvent solution of a compound represented by general formula (3):

$M^1 X_k$ where, $M^1$, X and k are the same as those described above.

The complex manufactured by the manufacturing method of the present invention is the compound represented by general formula (1) above and can manufacture not only the aforementioned complex in the present invention, but also a complex that contains bismuth as a metal species.

In general formula (1), X and L are the same as those described above. The same can apply to preferred embodiments.

In general formula (1), m represents a value of 0.3 to 2.8, which is more preferably 0.5 to 2.5, from the viewpoint of making the perovskite material more easily manufacturable, and more easily be improved in power conversion efficiency (PCE) and internal quantum efficiency (IQE). With Sn represented by $M^1$, m is likely to have a value of 0.3 to 1.9 (particularly 0.5 to 1.5), and with Bi represented by $M^1$, m is likely to have a value of 1.5 to 3.0 (particularly 1.7 to 2.8).

In general formulae (1) and (3), k represents a value of 1.5 to 3.5, which is more preferably 1.8 to 3.2, from the viewpoint of making the perovskite material more easily manufacturable, and more easily be improved in power conversion efficiency (PCE) and internal quantum efficiency (IQE). With Sn represented by $M^1$, k is likely to have a value of 1.5 to 2.5 (particularly 1.8 to 2.2), and with Bi represented by $M^1$, k is likely to have a value of 2.5 to 3.5 (particularly 2.8 to 3.2).

The compound represented by general formula (3) and preferably employable are exemplified by $SnI_2$, $SnBr_2$, $SnF_2$, and $BiI_3$.

Since the complex represented by general formula (1) is a complex comprising a compound having a predetermined chemical composition and polar solvent molecule as described above, a polar solvent solution of the compound represented by the aforementioned general formula (3) is used. The aforementioned polar solvent molecules are exemplified as the polar solvents for composing such solution. The same can apply to preferred embodiments. Since tin ion ($Sn^{2+}$) is very susceptible to oxidation in the presence of oxygen, the solution is preferably free of oxygen, and a polar solvent for used is preferably deaerated thoroughly. Only a single type of such polar solvent may be used independently, or two or more types may be used in a combined manner.

The higher the concentration of the compound represented by general formula (3) in the polar solvent solution is, the better the concentration of the compound is, from the viewpoint of easiness of obtaining the complex in the present invention. The concentration is preferably 1.0 to 10.0 mol/L, and is more preferably 2.0 to 6.0 mol/L. The polar solvent solution may be a saturated solution.

In the present invention, the complex represented by general formula (1) is manufactured by adding poor solubility solvent dropwise to the afore-mentioned polar solvent solution. Though the reaction mechanism is not necessarily elucidated, supposedly because concentration of the polar solvent becomes low locally at around the interface between the polar solvent solution and the poor solubility solvent or crystallization occurs rapidly, a polymerized complex in which polar solvent molecules are alternately coordinated is formed, keeping the structure of the compounds represented by general formula (3) to a certain degree. In this way, the complex represented by general formula (1) and composed of a needle crystal is formed. Obtained complex, when it is casted over a substrate to form a film, is likely to orient in the horizontal direction and to give a nearly flat film, owing to an effect of stress applied to the solution.

From the viewpoint of easiness of obtaining the complex represented by general formula (1), the poor solubility (for the complex) solvent is exemplified by substituted aliphatic hydrocarbons such as dichloromethane and chloroform; aromatic hydrocarbons such as toluene and benzene; substituted aromatic hydrocarbons such as chlorobenzene, orthodichlorobenzene and nitrobenzene; acetic acid; ethers such as diethyl ether, and tetrahydrofuran (THF); alcohols such as methanol, ethanol, isopropanol, butanol and octanol; long chain hydrocarbons (particularly C4-10 hydrocarbons) such as hexane; and acetonitrile. Only a single type of such poor solubility solvent may be used independently, or two or more types may be used in a combined manner. Among them, from the viewpoint of easiness of obtaining the complex in the present invention, the substituted hydrocarbons are preferable, and dichloromethane is more desirable.

Amount of addition of the poor solubility solvent is not specifically limited, but it is preferable, from the viewpoint of easiness of obtaining the complex in the present invention, to control the amount of addition of poor solubility solvent relative to the amount of consumption of polar solvent (poor solubility solvent/polar solvent) to (2.0 to 10.0)/1.0 (v/v), which is more preferably (3.0 to 8.0)/1.0 (v/v).

Note that from the viewpoint of easiness of obtaining the complex represented by general formula (1), it is preferable to filter and remove insolubles from the polar solvent solution.

From the viewpoint of easiness of isolation of the complex in the present invention, the content after addition of the poor solubility solvent is preferably allowed to stand for a long duration of time. For example, the content is preferably allowed to stand for about 5 to 100 hours, and particularly about 10 to 50 hours. On the other hand, in a case where the obtainable complex is produced in the process of film forming, and is used as an intermediate of a perovskite film with high flatness and high density, it is also possible to add the poor solubility solvent within a short time, followed by immediate heating (annealing), from the viewpoint of control of drying of the solvent.

While the reaction temperatures are not specifically limited and the reaction can be carried out under cooling, at room temperature, or under heating, the temperatures are preferably 30 to 100° C. in general, more preferably 40 to 80° C.

Thus obtainable complex represented by general formula (1) is exemplified by $SnI_2 \cdot DMF$, $3SnI_2 \cdot 2DMF$ ($SnI_2 \cdot (2/3)DMF$), $SnI_2 \cdot DMSO$, $SnBr_2 \cdot 2DMSO$, $SnBr_2 \cdot DMF$, $SnF_2 \cdot DMSO$, $4BiI_3 \cdot 8DMF$ ($BiI_3 \cdot 2DMF$, $Bi(DMF)_8 \cdot Bi_3I_{12}$), and $3BiI_3 \cdot 8DMSO$ ($BiI_3 \cdot (8/3)DMSO$, $Bi(DMSO)_8 \cdot Bi_2I_9$). Thus obtainable complex exemplified by general formula (1) is likely to be obtained in the form of needle microcrystal. The complex in the present invention, when formed as a film on a substrate, orients horizontally to the substrate, and is capable of yielding a nearly flat film.

3. Perovskite Compound and Manufacturing Method of Same

A perovskite compound in the present invention is represented by general formula (2A):

$RSnX_j$ where, Sn has an oxidation number of 1.5 to 2.5; R represents at least one type of monovalent cation; X represents at least one type of halogen atom; and j represents a value of 2.5 to 3.5, and being free of contamination with tin oxide; or represented by general formula (2B):

$R_2M^2BiX_i$ where, R and X are the same as those described above; $M^2$ represents a monovalent metal; and i represents a value of 5.0 to 7.0, and being free of contamination with bismuth oxide.

In general formulae (2A) and (2B), X is same as described above. The same can apply to preferred specific examples.

In general formulae (2A) and (2B), R represents at least one type of monovalent cation. As such monovalent cations, in addition to alkali metal cations or monovalent transition metal cations, cations represented by $R^1NH_3^+$, or

[Chemical Formula 3]

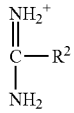

($R^2$ represents a hydrogen atom or monovalent substituted or unsubstituted hydrocarbon group) can also be exemplified. These cations may be contained only one type, or two or more types.

The alkali metal cation is exemplified by sodium cation, potassium cation, cesium cation, and rubidium cation.

The monovalent transition metal cation is exemplified by copper cation, silver cation, gold cation, iron cation, and ruthenium cation.

The monovalent hydrocarbon group represented by $R^1$ and $R^2$ is preferably an alkyl group having 1 to 10 carbon atoms, aryl group having 6 to 20 carbon atoms, and aralkyl group having 7 to 12 carbon atoms, more preferably alkyl group having 1 to 6 carbon atoms and aryl group having 6 to 14 atoms, and even more preferably alkyl group having 1 to 4 carbon atoms, from the viewpoint of making the perovskite material in the present invention more likely to have a three-dimensional structure, capable of absorbing light over wider wavelength ranges, and more likely to be improved in power conversion efficiency (PCE) and internal quantum efficiency (IQE). For the same reason, each of $R^1$ and $R^2$ preferably represents an alkyl group, which is more preferably a straight-chain or branched alkyl group, and even more preferably a straight-chain alkyl group. In particular, methyl group is most preferable.

As $R^1$ and $R^2$ described above, $R^1$ preferably represents a methyl group, and $R^2$ preferably represents a hydrogen atom, from the viewpoint of making the perovskite compound in the present invention more likely to have a three-dimensional structure, capable of absorbing light over wider wavelength ranges, and more likely to be improved in power conversion efficiency (PCE) and internal quantum efficiency (IQE). Other than an alkali metal cation and a monovalent transition metal cation, $CH_3NH_3^+$ or

[Chemical Formula 4]

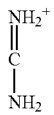

are preferably represented as R.

In general formula (2A), j represents a value of 2.5 to 3.5, which is more preferably 2.8 to 3.2, from the viewpoint of making it easier to improve power conversion efficiency (PCE) and internal quantum efficiency (IQE).

In general formula (2B), $M^2$ represents a monovalent metal. In general formula (2B), both of $M^2$ and Bi are metals that occupy the B-site of the perovskite compound, wherein monovalent metal is used as $M^2$ so as to compensate the valency of trivalent bismuth ion. Employable monovalent metal is exemplified by Na, K, Cu, Ag, and Au.

In general formula (2B), i represents a value of 5.0 to 7.0, which is more preferably 5.8 to 6.2, from the viewpoint of making it easier to improve power conversion efficiency (PCE) and internal quantum efficiency (IQE).

The perovskite compound in the present invention satisfying these conditions is exemplified by $CH_3NH_3SnI_3$ (occasionally referred to as "$MASnI_3$", hereinafter), $CH(NH_2)_2SnI_3$, $CsSnI_3$, and $CsSnBr3$.

The conventional lead-free perovskite compound demonstrates a metallic property, as a result of partial oxidation of tin ion ($Sn^{2+}$) into $Sn^{4+}$ for example. In contrast, in the perovskite compound in the present invention represented by general formula (2A), Sn keeps the oxidation number within the range from 1.5 to 2.5. In addition, unlike the conventional lead-free perovskite compound suffering from low purity due to contamination of tin oxide, the aforementioned perovskite compound in the present invention represented by general formula (2B) is free of tin oxide, and desirably has high purity.

Since the complex represented by general formula (1) is composed of a compound having a predetermined chemical composition and polar solvent molecule, so that the perovskite compound in the present invention is obtainable by reacting the complex with a desired compound, while releasing the polar solvent molecule. More specifically, the perovskite compound in the present invention may be obtained by a step of allowing:

the complex obtained by the aforementioned manufacturing method to react with;

a compound represented by general formula (4):

RX where, R and X are the same as those described above; and a compound represented, as needed, by general formula (5):

$M^2X$ where, $M^2$ and X are the same as those described above.

In general formula (4), R and X are the same as those described above. The same can apply to preferred specific examples.

$CH_3NH_3I$ (occasionally referred to as "MAI", hereinafter), $CH(NH_2)_2I$, and CsI, for example, are preferably employed as the compound represented by general formula (4).

While the amount of addition of the compound represented by general formula (4) is not specifically limited, the amount of addition per 1 mol of the complex represented by general formula (1) is preferably 0.5 to 2.0 mol (particularly 0.8 to 1.3 mol) from the viewpoint of easiness of obtaining the perovskite compound in the present invention when intended to obtain the perovskite compound represented by general formula (2A), and is preferably 1.0 to 3.0 mol (particularly 1.5 to 2.5 mol) when intended to obtain the perovskite compound represented by general formula (2B).

Next, in the perovskite compound represented by general formula (2B), a monovalent metal is used as $M^2$ so as to compensate the valency of trivalent bismuth ion. Hence, the compound represented by general formula (5) is also used for manufacturing the perovskite compound represented by general formula (2B).

In general formula (5), $M^2$ and X are the same as those described above. The same can apply to preferred specific examples.

NaI, KI, CuI, AgI, and AuI, for example, are preferably employable as the compound represented by general formula (5).

While the amount of addition of the compound represented by general formula (5), when used, is not specifically limited, the amount of addition is, from the viewpoint of easiness of obtaining the perovskite compound in the present invention, preferably 0.5 to 2.0 mol, and more preferably 0.8 to 1.3 mol, per 1 mol of the complex represented by general formula (1).

The aforementioned reaction is preferably carried out in a polar solvent. The polar solvent employable here is not specifically limited, and may be any of those described previously. The same can apply to preferred embodiments. In particular, from the viewpoint of making the complex represented by general formula (1) more soluble and improved in the productivity, it is preferable to use a same kind of polar solvent as the polar solvent molecule contained in the complex represented by general formula (1). Since, however, tin ion (Sn') is very susceptible to oxidation in the presence of oxygen, the solution is preferably free of oxygen, and a polar solvent for used is preferably deaerated thoroughly. Only a single type of such polar solvent may be used independently, or two or more types may be used in a combined manner.

Note that it takes a long time to dissolve a commercially available tin halide or bismuth halide, when used as a starting material, into the polar solvent, whereas the complex represented by general formula (1), when used as a starting material, may be dissolved within several minutes. Hence according to the present invention, it is also possible to improve the productivity.

In a case where the aforementioned reaction is carried out in the polar solvent, concentrations of the individual compounds are preferably as follows, from the viewpoint of easiness of obtaining the complex in the present invention. More specifically, the concentration of the complex represented by general formula (1) is preferably 1.0 to 5.0 mol/L (particularly, 1.5 to 3.0 mol/L). When one intends to obtain the perovskite compound represented by general formula (2A), the concentration of the compound represented by general formula (4) is preferably 1.0 to 5.0 mol/L (particularly, 1.5 to 3.0 mol/L). Moreover, when one intends to obtain the perovskite compound represented by general formula (2B), the concentration of the compound represented by general formula (4) is preferably 2.0 to 10.0 mol/L (particularly, 3.0 to 5.0 mol/L), and the concentration of the compound represented by general formula (5) is preferably 1.0 to 5.0 mol/L (particularly, 1.5 to 3.0 mol/L).

The polar solvent molecule in the complex represented by general formula (1), although less likely to be released at normal temperature, may easily be released by heating. Take $SnI_2 \cdot DMF$ as an example, heating at approximately 70° C. or above induces release of the polar solvent molecule, and dissolves into released polar solvent. For easier release of the polar solvent molecule in the complex represented by general formula (1), the aforementioned reaction is preferably carried out under heating. Reaction temperature is preferably 80 to 200° C., and more preferably 90 to 150° C. Reaction time is preferably 10 minutes to 6 hours, and more preferably 30 minutes to 3 hours. As a specific operation, it is preferable to be coated (typically by drop casting), over a substrate heated at a desired temperature, with a polar solvent solution that contains the complex represented by general formula (1), the compound represented by general formula (4), and the compound represented, as needed, by general formula (5).

The substrate is not specifically limited, so long as it can be coated with the polar solvent solution. Also materials composing substrate are not specifically limited so long as the purpose of the present invention will not be adversely affected, allowing any one of known substrates to be employed. For example, any one of glass substrate, insulator substrate, semiconductor substrate and electroconductive substrate (including electroconductive film) is employable. Also these substrates having formed partially or entirely on their surfaces at least one type of film selected from metal film, semiconductor film, electroconductive film and insulating film can be used preferably.

Metal that composes the metal film is one type of, or two or more types of metals selected, for example, from gallium, iron, indium, aluminum, vanadium, titanium, chromium, rhodium, nickel, cobalt, zinc, magnesium, calcium, silicon, yttrium, strontium and barium. Material that composes the semiconductor film is exemplified by simple element such as silicon and germanium; compounds containing Groups III to V elements or Groups XIII to XV elements in the periodic table; metal oxides; metal sulfides; metal selenides; and metal nitrides. Also, material that composes the electroconductive film is exemplified by tin-doped indium oxide (ITO), fluorine-doped indium oxide (FTO), zinc oxide (ZnO), aluminum-doped zinc oxide (AZO), gallium-doped zinc oxide (GZO), tin oxide ($SnO_2$), indium oxide ($In_2O_3$) and tungsten oxide ($WO_3$). Material that composes the insulating film is exemplified by aluminum oxide ($Al_2O_3$), titanium oxide ($TiO_2$), silicon oxide ($SiO_2$), silicon nitride ($Si_3N_4$) and silicon oxynitride ($Si_4O_5N_3$).

The substrate may have any form and may be effective in any form, including plate form such as flat plate or disk, fiber form, rod form, column form, prism form, cylinder form, spiral form, sphere form and ring form. Also, a porous structure may be employed. In the present invention, the substrate preferably has a plate form. Thickness of the substrate is preferably, but not specifically limited to, 0.1 μm to 100 mm, and is more preferably 1 μm to 10 mm.

Note that from the viewpoint of easiness of obtaining the perovskite compound in the present invention, the polar solvent solution is preferably filtered to be freed from insoluble matter, before reacting (heating).

4. Perovskite Layer (Perovskite Layer for Perovskite Solar Cell) and Perovskite Solar Cell While the complex in the present invention and the complex represented by general formula (1) are fine needle crystals as described above, films composed of the complex in the present invention and the complex represented by general formula (1) are nearly flat films. Since the perovskite compound obtained by using the complex in the present invention and the complex represented by general formula (1), when formed into a nearly flat perovskite layer, contains a high purity of tin ion ($Sn^{2+}$) or bismuth ion ($Bi^{3+}$) and highly stable, so that solar cell characteristics (particularly photoelectric conversion efficiency) of the perovskite solar cell may be improved.

The perovskite solar cell in the present invention may have a structure same as that of the known perovskite solar cells, except having a perovskite layer composed of the complex in the present invention, the complex represented by general formula (1), or the perovskite compound in the present invention, as the perovskite layer (light absorbing layer). For example, the perovskite solar cell in the present invention preferably has a transparent electrode, a (hole) blocking layer, an electron transport layer, the perovskite layer (light absorbing layer), a hole transport layer, and a metal layer in this order.

(4-1) Transparent Electrode

Since the transparent electrode serves as a support for the (hole) blocking layer, as well as a layer capable of extracting electric current (electrons) through the (hole) blocking layer from the perovskite layer (light absorbing layer), so that the transparent electrode is preferably composed of an electroconductive substrate, and is preferably a transparent electroconductive layer with translucency capable of permitting transmission of light that takes part in photoelectric conversion.

The transparent electroconductive layer is exemplified by tin-doped indium oxide (ITO) film, impurity-doped indium oxide ($In_2O_3$) film, impurity-doped zinc oxide (ZnO) film, fluorine-doped tin dioxide (FTO) film, and stacked film of these films.

Thickness of these transparent electroconductive films is not specifically limited, it is preferably determined so as to generally adjust the resistance 5 to 15 Ω/□.

The transparent electroconductive layer may be obtained by any of known film forming methods, depending on materials to be formed.

The transparent electroconductive layer may optionally be covered with a translucent cover material for external protection.

The translucent cover material is exemplified by resin sheets made of fluorine-containing resin, polyvinyl chloride, polyimide and so forth; inorganic sheets made of white glass, soda glass and so forth; and hybrid sheets based on combination of these materials.

Thickness of these translucent cover materials is not specifically limited, it is preferably determined so as to generally adjust the resistance 5 to 15 Ω/□.

(4-2) (Hole) Blocking Layer

The (hole) blocking layer is provided to improve solar cell characteristics (particularly photoelectric conversion efficiency) through prevention of hole leakage and suppression of reverse current, and is preferably provided between the transparent electrode and the perovskite layer (light absorbing layer). The (hole) blocking layer is preferably a layer made of metal oxide such as titanium oxide, and is more preferably a layer made of n-type semiconductor such as compact $TiO_2$, covering the surface of transparent electrode in a smooth and dense manner. Now the term "dense" means that the packing density of a metal compound is higher than the packing density of a metal compound in the electron transport layer. Note that there may be pinholes and cracks, so long as the transparent electrode and the electron transport layer are not electrically connected therethrough.

The (hole) blocking layer is 5 to 300 nm thick for example. From the viewpoint of electron injection efficiency into the electrode, the (hole) blocking layer is more preferably 10 to 200 nm thick.

The (hole) blocking layer is formed over the transparent electrode layer. The (hole) blocking layer, when composed of a metal oxide, is manufacturable by any of known methods such as spray pyrolysis (for example, Non-Patent Literature 4, J. Phys. D: Appl. Phys. 2008, 41, 102002, etc.). The (hole) blocking layer is manufacturable, typically by spraying a 0.01 to 0.40 M (particularly 0.02 to 0.20 M) alcohol solution (for example, isopropanol solution) of a metal alkoxide (such as titanium diisopropoxide bis(acetylacetonate)), over the transparent electrode placed on a hot plate heated at 200 to 550° C. (particularly 300 to 500° C.).

After that the film may further be densified, by immersing and heating the obtained substrate in an aqueous solution of titanium oxide ($TiO_2$, etc.), titanium alkoxide (titanium isopropoxide, etc.) or titanium halide ($TiCl_4$, etc.).

The aqueous solution preferably has a concentration of 0.1 to 1.0 mmol/L, which is more preferably 0.2 to 0.7 mmol/L. Immersion temperature is preferably 30 to 100° C., and more preferably 50 to 80° C. Heating conditions are preferably 200 to 1000° C. (particularly 300 to 700° C.) for 5 to 60 minutes (particularly 10 to 30 minutes).

(4-3) Electron Transport Layer

The electron transport layer is formed in order to increase active surface area of the perovskite layer (light absorbing layer), to improve the photoelectric conversion efficiency, and to facilitate collection of electrons. The electron transport layer is preferably formed over the (hole) blocking layer.

The electron transport layer, considering that it is formed over the perovskite layer, might be a flat layer using an organic semiconductor material such as fullerene derivative, but preferably has a porous structure. The porous structure is preferably formed typically by gathering of granular material, needle like material, tubular material or columnar material, demonstrating a porous property as a whole. Pore size is preferably on a nanometer scale. With the porous structure on the nanometer scale, the light absorbing layer will have a considerably increased active surface area, will be improved in the solar cell characteristics (particularly photoelectron conversion efficiency), and will therefore be a porous electron transport layer that works well in electron collection.

The electron transport layer is preferably a layer composed of a metal oxide such as titanium oxide. In a case that semiconductor is used, where the metal compound is a semiconductor, donor may be doped. In this way, the electron transport layer can serve as a window layer through which light is introduced into the perovskite layer (light absorbing layer), and can extract electric power from the perovskite layer (light absorbing layer) in more efficient manner.

While thickness of the electron transport layer is not specifically limited, it is preferably around 10 to 300 nm, more preferably around 10 to 250 nm from the viewpoint of efficiently collecting electrons from the perovskite layer (light absorbing layer).

The electron transport layer may be formed by any of known film forming methods, depending on materials to be formed. For example, the electron transport layer may be formed by coating alcohol solution (ethanol solution, for example) containing 5 to 50% by mass (particularly 10 to 30% by mass) of a titanium oxide paste over the (hole) blocking layer. The titanium oxide paste employable here may be any of known or commercially available products. Method of coating is preferably spin coating. The coating may be carried out typically at around 15 to 30° C.

(4-4) Perovskite Layer (Light Absorbing Layer)

The perovskite layer (light absorbing layer) in the perovskite solar cell is a layer that executes photoelectric conversion by absorbing light and allowing excited electrons to migrate therethrough. The perovskite layer (light absorbing layer) is a layer that contains the perovskite compound using the complex in the present invention or the complex represented by general formula (1), or a layer comprises perovskite compound in the present invention. It enables the perovskite layer to be very flat and improve power conversion efficiency (PCE) and internal quantum efficiency (IQE). In addition, the perovskite layer may be a layer composes a perovskite compound with high elemental purity.

Since the present invention is applicable to mass production based on a roll-to-roll process, the mixed liquid may be coated over the substrate by spin coating, dip coating, screen printing, roll coating, die coating, transfer printing, spray coating or slit coating and the like, preferably by spin coating. The substrate may be any of those described above.

While the perovskite layer (light absorbing layer) in the present invention may be formed over various types of substrate as described above, it is convenient to form the layer over the electron transport layer.

The perovskite layer may be: a layer solely composed of the perovskite compound obtained from the complex in the present invention or the complex represented by general formula (1), or the perovskite compound in the present invention; or a layer that contains a metal oxide, such as mesocrystalline titanium oxide or aluminum oxide, and the perovskite compound from a viewpoint of adhesiveness with the (hole) blocking layer.

Thickness of the perovskite layer (light absorbing layer) is, for example, preferably 50 to 1000 nm, more preferably 200 to 800 nm from the viewpoints of balance between the light absorption efficiency and exciton diffusion length, and of absorption efficiency of light reflected on the transparent electrode. The thickness of the perovskite layer (light absorbing layer) in the present invention is measured by cross-sectional scanning electron microscopy (cross-sectional SEM) of a film composed of the complex in the present invention.

Method of film forming of the perovskite layer (light absorbing layer) is not specifically limited, and may be any of ordinary methods. For example, the perovskite compound in the present invention, also when obtained by the manufacturing method of the present invention, is obtainable in the form of perovskite layer. The perovskite layer (light absorbing layer) may alternatively be obtained by dissolving the perovskite compound in the present invention into an organic solvent, followed by spin coating.

(4-5) Hole Transport Layer

The hole transport layer is a layer comprising functions to transport electric charge. As the hole transport layer, for example, electric conductor, semiconductor, organic hole transport material, and so forth can be used. Such material can function as a hole transport material that accepts hole from the perovskite layer (light absorbing layer) and transports the hole. The hole transport layer is formed over the perovskite layer (light absorbing layer).

The electric conductor and semiconductor are exemplified, for example, by compound semiconductors containing monovalent copper such as CuI, $CuInSe_2$ and CuS; and compounds containing metals other than copper, such as GaP, NiO, CoO, FeO, $Bi_2O_3$, $MoO_2$, and $Cr_2O_3$. Among them, from the viewpoint of selectively accepting hole in a more efficient manner, and of obtaining higher hole mobility, the semiconductor containing monovalent copper is preferable, and CuI is more preferable.

The organic hole transport material is exemplified by polythiophene derivatives such as poly-3-hexylthiophene (P3HT) and polyethylene dioxythiophene (PEDOT); fluorene derivatives such as 2,2',7,7'-tetrakis-(N,N-di-p-methoxyphenylamine)-9,9'-spirobifluorene (spiro-OMeTAD); carbazole derivatives such as polyvinyl carbazole; triphenylamine derivatives such as poly[bis(4-phenyl)(2,4,6-trimethylphenyl)amine] (PTAA); diphenylamine derivatives; polysilane derivatives; and polyaniline derivatives. Among them, from the viewpoint of selectively accepting hole in a more efficient manner, and of obtaining higher hole mobility, triphenylamine derivatives, fluorene derivatives, and so forth are preferable, and PTAA and spiro-OMeTAD are more preferable.

In the hole transport layer, for the purpose of further improving the hole transport characteristics, an oxidant such as lithium bis(trifluoromethylsulfonyl)imide (LiTFSI), silver bis(trifluoromethylsulfonyl)imide, trifluoromethylsulfonyloxy silver, $NOSbF_6$, $SbCl_5$, $SbF_5$, and so forth can be contained. In the hole transport layer, a basic compound such as tert-butylpyridine (TBP), 2-picoline, and 2,6-lutidine can also be contained. Content of the oxidant and the basic compound can be the same as those used in the conventional practice.

Thickness of the hole transport layer is, for example, preferably 30 to 200 nm, more preferably 50 to 100 nm, from the viewpoint of selectively accepting holes in a more efficient manner and achieving a higher hole mobility.

It is preferable that method of film forming of the hole transport layer takes place, for example, in a dry atmosphere. For example, it is preferable to be coated (spin-coat, for example) with a solution containing an organic hole transport material, over the perovskite layer (light absorbing layer) in a dry atmosphere, followed by heating at 30 to 150° C. (particularly 50 to 100° C.).

(4-6) Metal Electrode

The metal electrode, when disposed so as to be opposed with the transparent electrode and formed over the hole transport layer, can donate and accept electric charge to and from the hole transport layer.

Any of materials known in the art can be used as a material for composing the metal electrode, and is exemplified by metals such as platinum, titanium, stainless steel, aluminum, gold, silver, and nickel, or alloys of these metals.

Among them, materials that can be formed typically by vapor deposition are preferable for the metal electrode, since the electrode can be formed in a dry atmosphere.

Also, perovskite solar cells having structures other than the aforementioned layer structures may be manufactured in the same way.

EXAMPLES

The present invention will further be detailed below referring to Examples and so forth. The present invention is, however, not limited to these Examples. X-ray structural analysis was conducted using Sheldrick, G. M. SHELX-97, Program for the Refinement of Crystal Structures; University of Gottingen: Gottingen, Germany, 1997.

Reference Example 1: Sublimation Purification of Commercially Available $SnI_2$

Figure 2:
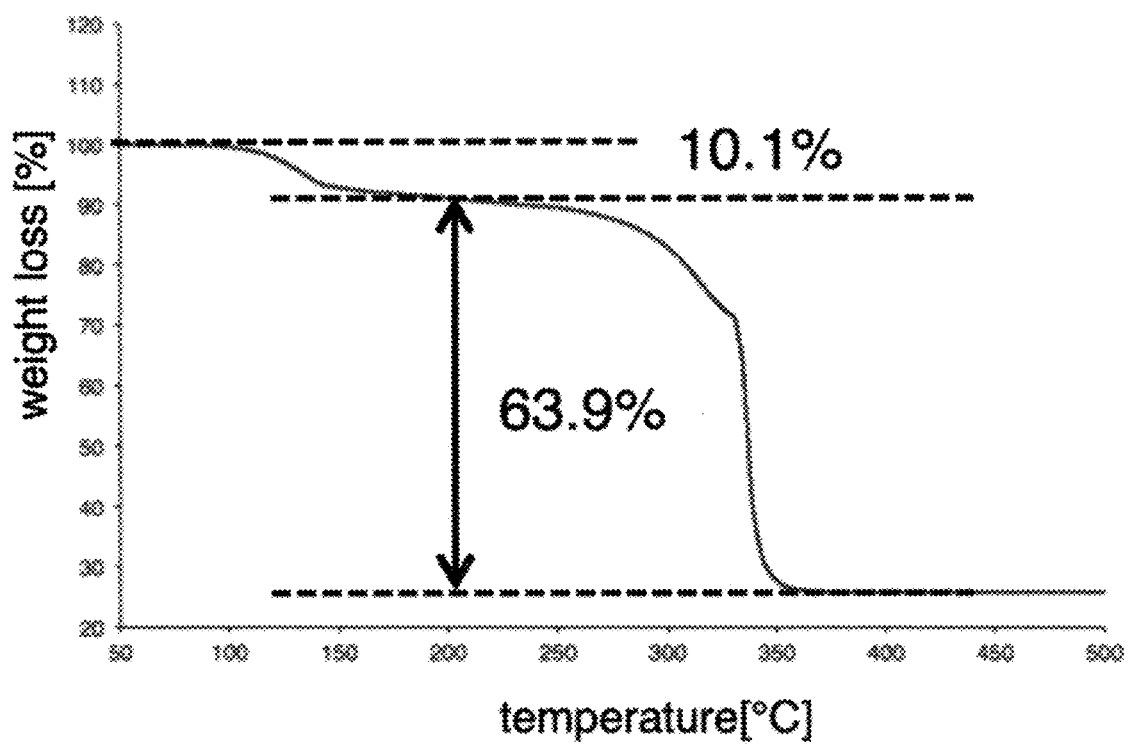
FIG. 2 illustrates a result of TGA measurement of $SnI_2$ used as a starting material in Reference Example 1.

Results of measurements, by $^{119}Sn$ MAS NMR and TGA, of $SnI_2$ (99.9% trace metal basis, from Kojundo Chemical Lab. Co., Ltd.) used as a starting material are shown in FIGS. 1 and 2.

Figure 3:
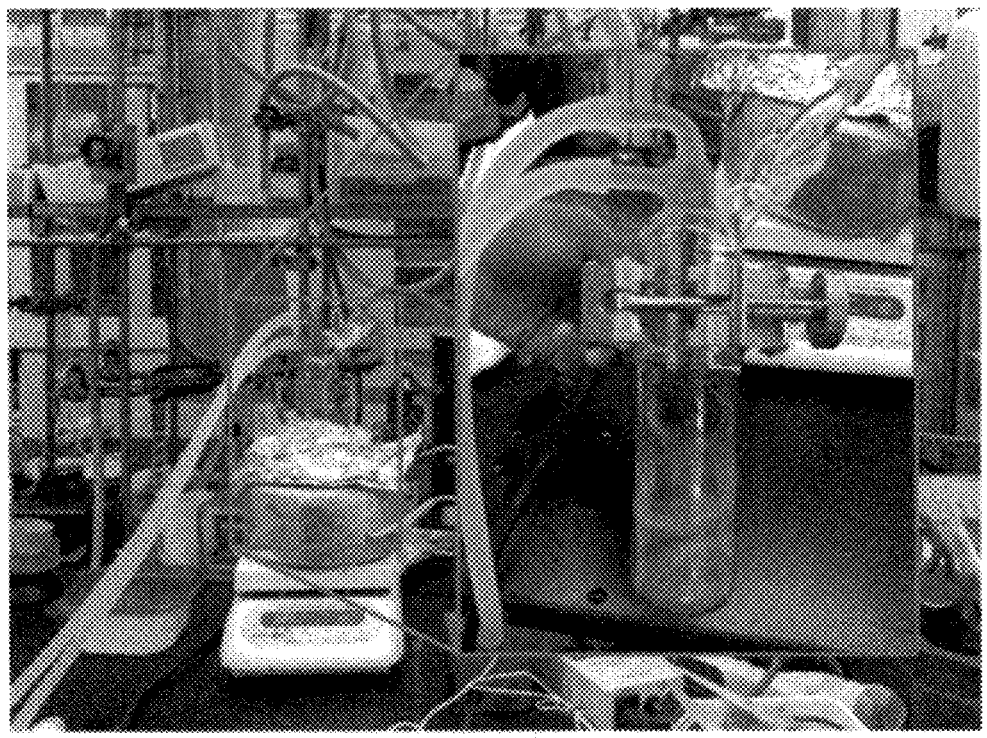
FIG. 3 illustrates a sublimation purification apparatus used in Reference Example 1.
Figure 4:
FIG. 4 illustrates a state of the sublimation purification apparatus after sublimation purification in Reference Example 1.
Figure 5:
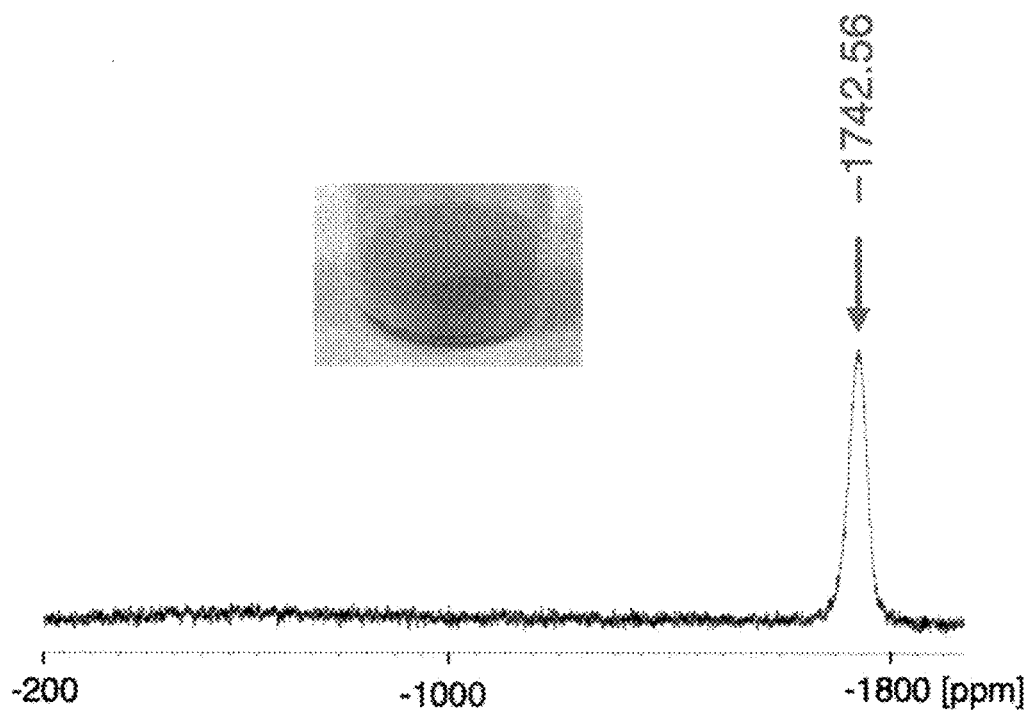
FIG. 5 is a $^{119}$Sn MAS NMR spectrogram of a compound (1st sublime) obtained in Referential Example 1.
Figure 6:
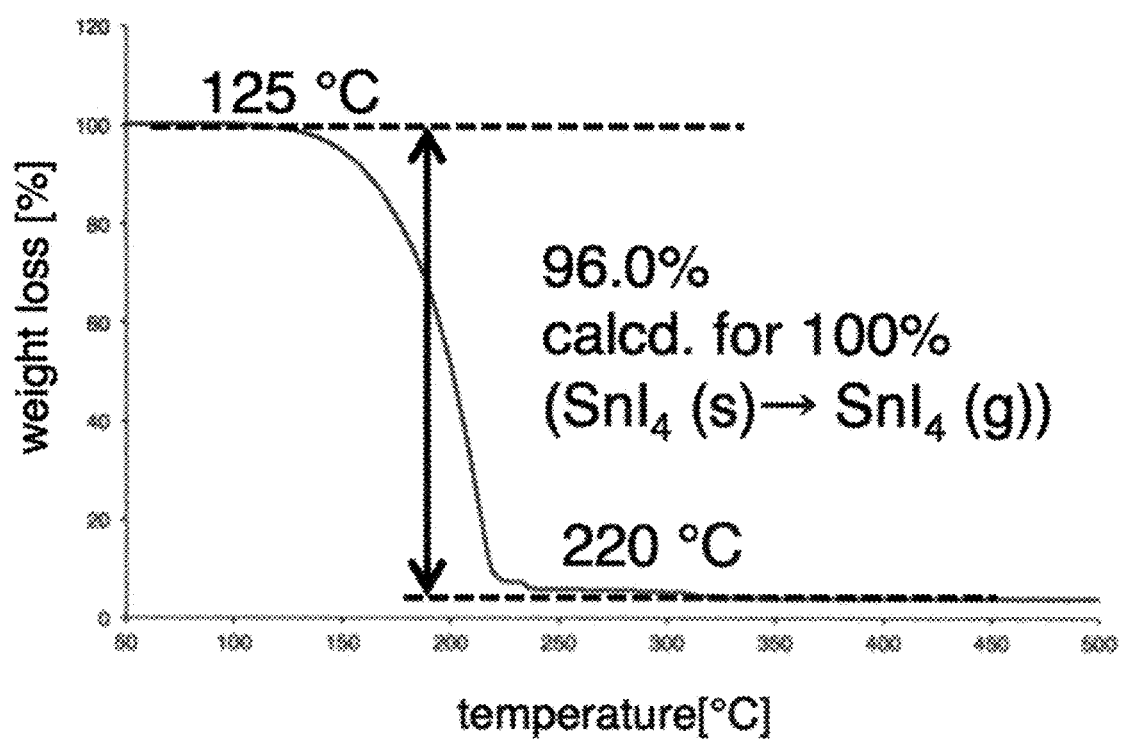
FIG. 6 illustrates a result of TGA measurement of the compound (1st sublime) obtained in Referential Example 1.
Figure 7:
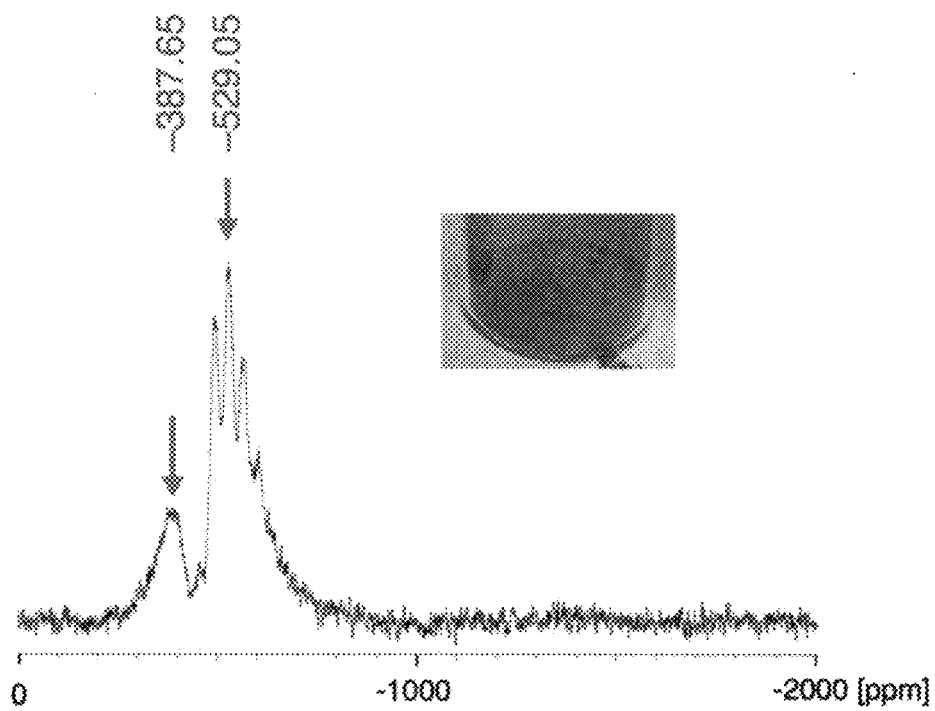
FIG. 7 is a $^{119}$Sn MAS NMR spectrogram of a compound (2nd sublime) obtained in Referential Example 1.
Figure 8:
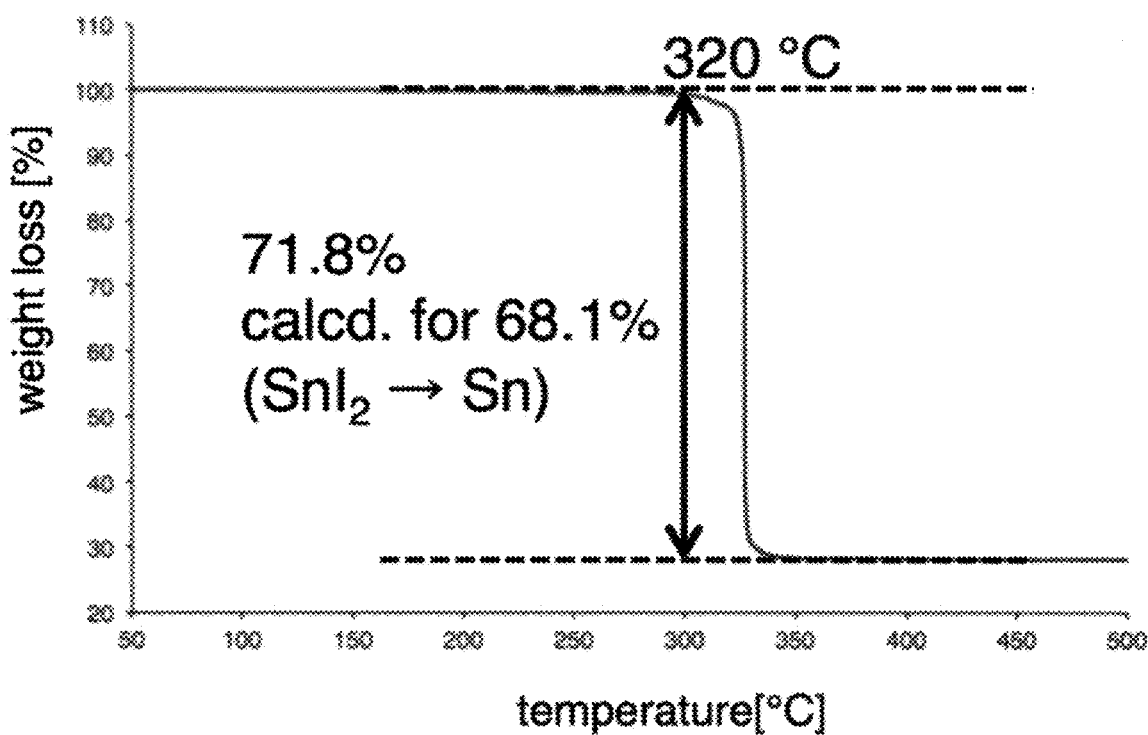
FIG. 8 illustrates a result of TGA measurement of the compound (2nd sublime) obtained in Referential Example 1.

Next, 10.68 g of $SnI_2$ (99.9% trace metal basis, from Kojundo Chemical Laboratory Co., Ltd.) was placed in a sublimation purification apparatus illustrated in FIG. 3, and the apparatus was evacuated (100 Pa) at normal temperature. The sublimation purification apparatus was then placed in a mantle heater, and kept under reduced pressure (0.5 mmHg) at 150° C. for 10 hours, to obtain 2.09 g of $SnI_4$ as a red crystal (1st sublime). The apparatus was then kept at 330° C. for 22 hours under a reduced pressure (0.5 mmHg), cooled down to room temperature, a container was then transferred to a globe box (Ar gas), to obtain 7.12 g of $SnI_2$ as a red crystalline sublimate (2nd sublime). The state after sublimation purification is shown in FIG. 4. Obtained compounds (1st sublime and 2nd sublime) were subjected to measurements by solid-state NMR and TGA (FIGS. 5 to 8).

From the results, it is understood that the commercially available $SnI_2$, even with a nominal purity of 99.9%, is a mixture of $SnI_2$ and $SnI_4$, in which $SnI_4$ accounts for around 10% by mass, since $SnI_4$ sublimed at 150° C., and $SnI_2$ sublimed at 330° C. Meanwhile, the sublimation purified product (2nd sublime) was understood to be a high purity $SnI_2$, since it showed weight loss in TGA only at around 320° C. In short, it is suggested that an effort of synthetizing a perovskite compound from a commercially available product will fail in obtaining stable performances due to abundance of impurities, need sublimation purification before use, and the durability is even less when used for assembling the solar cell.

Example 1: $SnI_2 \cdot DMF$

Figure 9:
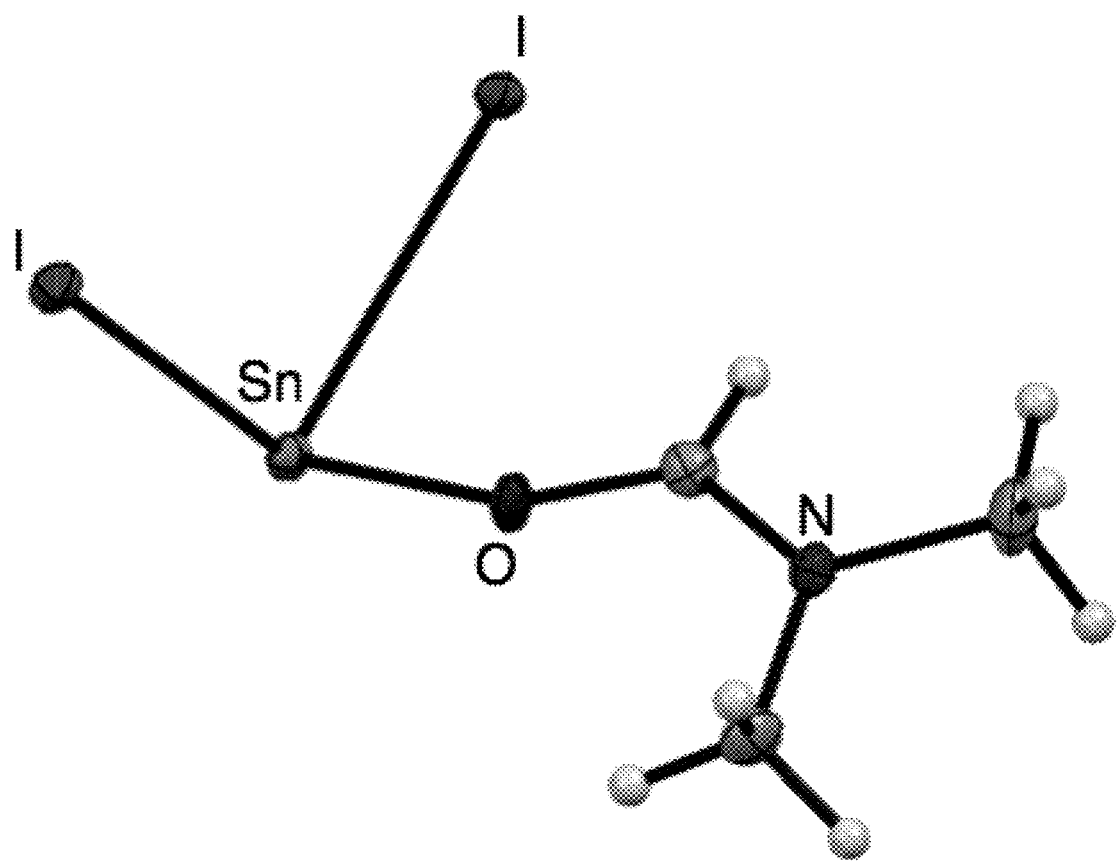
FIG. 9 illustrates a result (ORTEP chart) of single crystal X-ray crystallography of a compound ($SnI_2 \cdot DMF$) obtained in Example 1, showing an $SnI_2$ molecule on the left, and a DMF molecule on the right.
Figure 10:
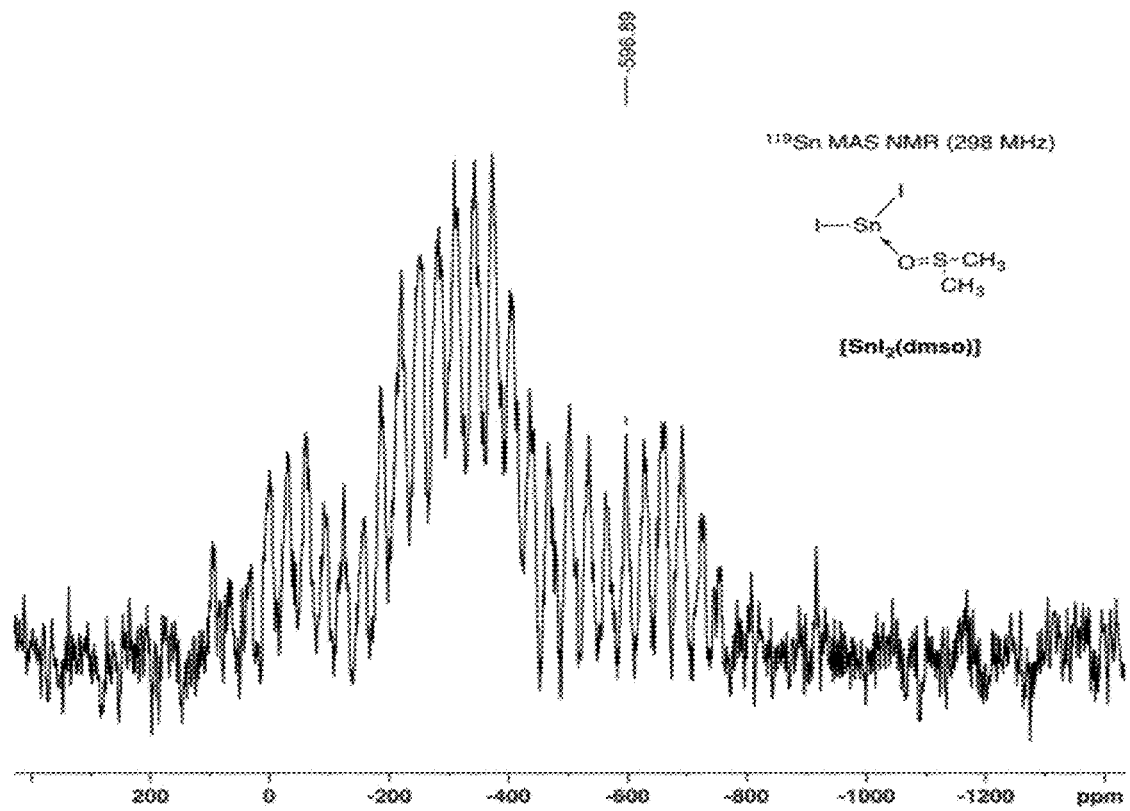
FIG. 10 is a $^{119}$Sn MAS NMR spectrogram of the compound ($SnI_2 \cdot DMF$) obtained in Example 1.

In a globe box, $SnI_2$ (4470 mg, 12 mmol; sublimation purified product, from Tokyo Chemical Industry Co., Ltd.) was allowed to dissolve into super dehydrated DMF (3 mL; from Wako Pure Chemical Company) at 50° C. The mixture remained in the form of suspension even after being stirred for one hour, rather than being completely dissolved. Remaining insoluble matter was removed by filtration using a PTFE filter, the filtrate was transferred into a test tube with a screw cap, approximately 15 mL of methylene chloride as a poor solubility solvent was slowly added thereto, and the content was allowed to recrystallize by the double layer diffusion method. Two days after, $SnI_2 \cdot DMF$ was obtained as a colorless needle crystal. Yield was 72% (3876 mg, 8.7 mmol). Obtained single crystal was analyzed by single crystal X-ray crystallography, to clarify the detailed structure (FIG. 9).

mp: 68.5-75.0° C.; $^{119}Sn$ MAS NMR (298 MHz): δ −391.08 (FIG. 10). Crystal data: $C_3H_7I_2NOSn$; FW=445.59, crystal size 0.11×0.11×0.09 mm, Monoclinic, $P2_1/c$, a=4.4957(4) Å, b=16.2298(14) Å, c=12.5040(11) Å, β=95.2852(11°), V=908.47(14) Å$^3$, Z=4, $D_c$=3.258 g/cm$^3$. The refinement converged to $R_1$=0.0164, $wR_2$=0.0379 (I>2σ (I)), GOF=1.049.

Example 2: $3SnI_2 \cdot 2DMF$

In a globe box, $SnI_2$ (4.3 g, 11.7 mmol; sublimation purified product, from Tokyo Chemical Industry Co., Ltd.)

was allowed to dissolve into super dehydrated DMF (2.9 mL; from Wako Pure Chemical Company) at 50° C. The mixture remained in the form of suspension even after being stirred for one hour, rather than being completely dissolved. Remaining insoluble matter was removed by filtration using a PTFE filter, the filtrate was transferred into a test tube with a screw cap, approximately 15 mL of methylene chloride as a poor solubility solvent was slowly added thereto, and the content was allowed to recrystallize by the double layer diffusion method. One day after, $3SnI_2 \cdot 2DMF$ was obtained as an orange needle crystal. Yield was 30% (1.2 g, 0.9 mmol).

Figure 11:
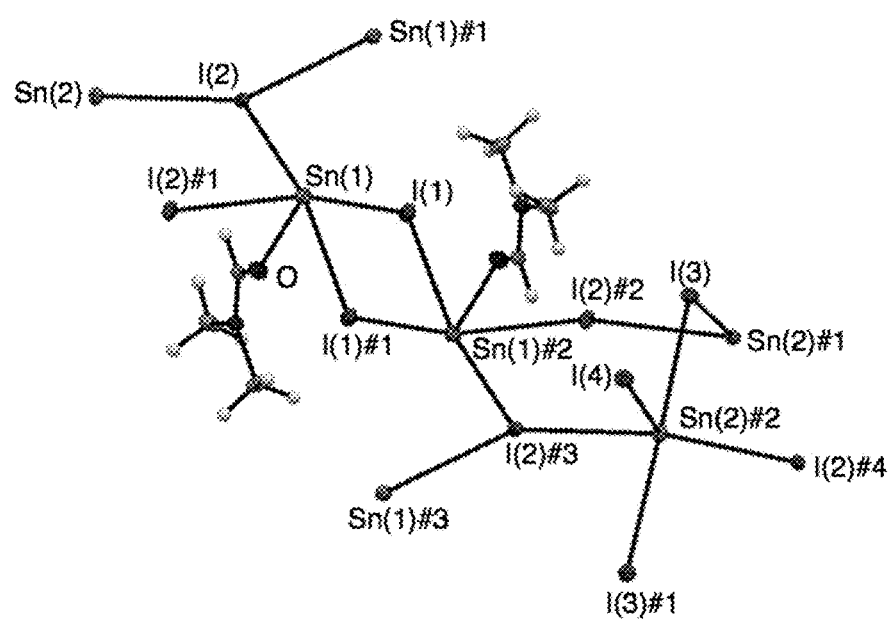
FIG. 11 illustrates a result (ORTEP chart) of single crystal X-ray crystallography of a compound ($3SnI_2.2DMF$) obtained in Example 2.

Obtained single crystal was analyzed by single crystal X-ray crystallography, to clarify the detailed structure (FIG. 11).

Crystal data: $C_6H_{14}I_6N_2O_2Sn_3$; FW=1263.52, crystal size 0.02×0.06×0.08 mm, Orthorhombic, Pnma, a=9.1107(11) Å, b=27.437(3) Å, c=9.1779(11) Å, V=2294.2(5) Å$^3$, Z=8, $D_c$=3.659 g/cm$^3$. The refinement converged to $R_1$=0.0140, $wR_2$=0.0262 (I>2σ(I)), GOF=1.119.

Comparative Example 1: $MASnI_3$ (Started from $SnI_2$ Just as Sublimation Purified)

In a globe box, $SnI_2$ (745 mg, 2 mmol; sublimation purified product, from Tokyo Chemical Industry Co., Ltd.) and MM (318 mg, 2 mmol; from Tokyo Chemical Industry Co., Ltd.) were allowed to dissolve into super dehydrated DMF (1 mL; from Wako Pure Chemical Company) at 50° C. After being stirred for one hour, the content was filtered through a PTFE filter. The filtrate was transferred into a test tube with a screw cap, and approximately 5 mL of methylene chloride as a poor solubility solvent was slowly poured. Several days after, a single crystal of $MASnI_3$ was obtained as a black crystal. The crystal was confirmed to be $MASnI_3$ by X ray crystallography, on the basis of coincidence with literature data.

Measured data: Cubic, Pm-3m, a=6.21 Å, V=240 Å$^3$. Literature data[1]: Cubic, Pm-3m, a=6.2461(2) Å, V=243.684(14) Å$^3$. [ref 1] Xutang Tao et. al., Angew. Chem. Int. Ed., 2016, 55, 3447.

Example 3: $MASnI_3$ (Started from $SnI_2 \cdot DMF$ of Example 1)

Figure 12:
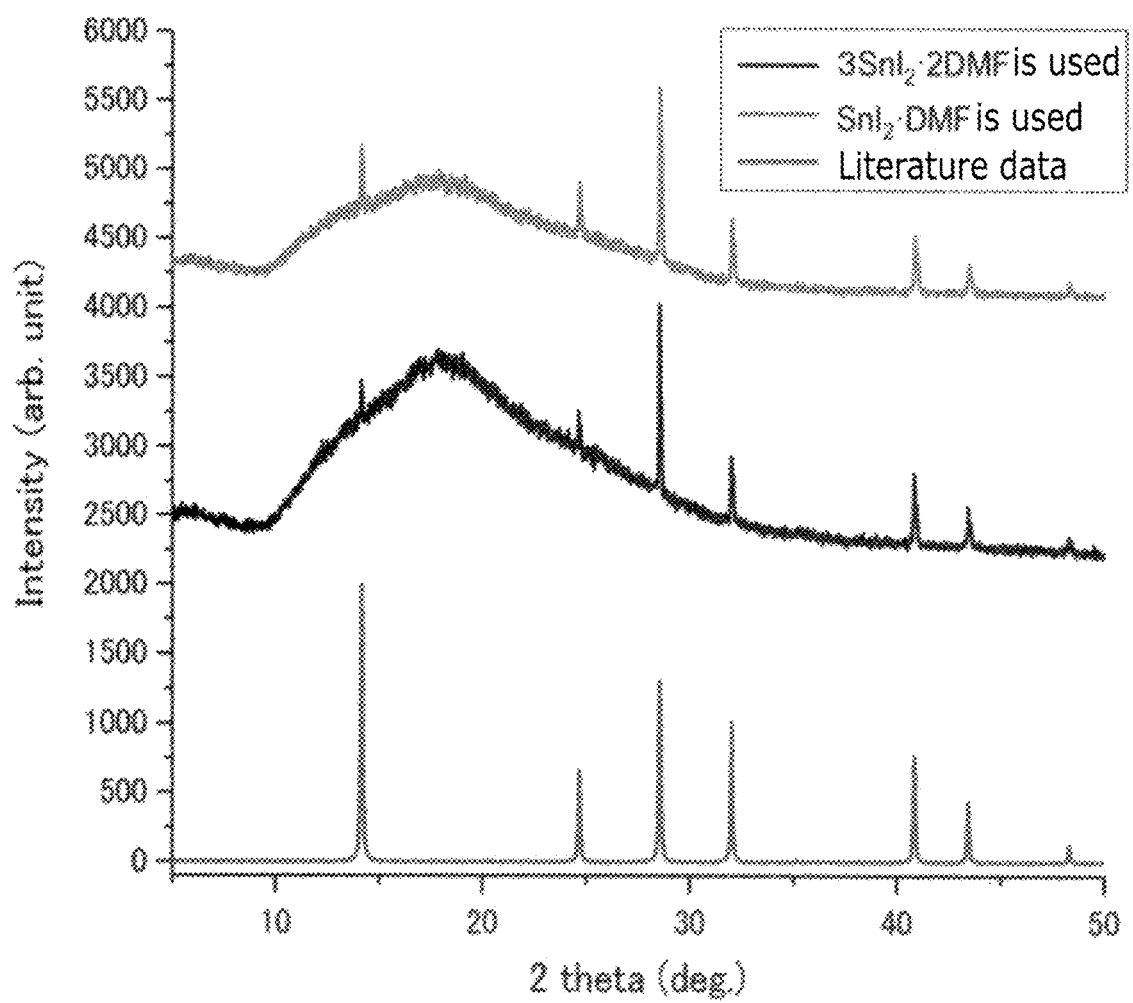
FIG. 12 illustrates powder X-ray diffraction spectra of compounds ($MASnI_3$) obtained in Examples 3 and 4, as well as literature data for reference.

In a globe box, $SnI_2 \cdot DMF$ (166 mg, 0.37 mmol) obtained in Example 1, and MM (59 mg, 0.37 mmol; from Tokyo Chemical Industry Co, Ltd.) were allowed to dissolve into super dehydrated DMF (185 µL; from Wako Pure Chemical Company) at 50° C. After being stirred for 5 minutes (the content was successfully dissolved within a very short time, unlike Comparative Example 1), the content was filtered through a PTFE filter. The filtrate was then drop cast on a slide glass kept at 110° C., to obtain a black solid. After heated for one hour, the obtained black solid was collected, subjected to powder XRD (FIG. 12), and confirmed to be $MASnI_3$, on the basis of coincidence with literature data.

Measured data: 2 theta=14.1, 24.6, 28.5, 32.0, 40.8, 43.4, 48.3. Literature data[2]: 2 theta=14.2, 24.7, 28.6, 32.0, 40.9, 43.3, 48.3. [ref 2] Tamotsu Inabe et. al., Dalton Trans., 2011, 40, 5563.

Example 4: $MASnI_3$ (Started from $3SnI_2 \cdot 2DMF$ of Example 2)

In a globe box, $3SnI_2 \cdot 2DMF$ (284 mg, 0.23 mmol) obtained in Example 2, and MM (107 mg, 0.68 mmol; from Tokyo Chemical Industry Co, Ltd.) were allowed to dissolve into super dehydrated DMF (183 µL; from Wako Pure Chemical Company) at 50° C. After being stirred for 5 minutes (the content was successfully dissolved within a very short time, unlike Comparative Example 1), the content was filtered through a PTFE filter. The filtrate was then drop cast on a slide glass kept at 110° C., to obtain a black solid. After heated for one hour, the obtained black solid was collected, subjected to powder XRD (FIG. 12), and confirmed to be $MASnI_3$, on the basis of coincidence with literature data.

Measured data: 2 theta=14.2, 24.7, 28.6, 32.0, 40.9, 43.5, 48.3. Literature data[2]: 2 theta=14.2, 24.7, 28.6, 32.0, 40.9, 43.3, 48.3. [ref 2] Tamotsu Inabe et. al., Dalton Trans., 2011, 40, 5563.

Test Example 1: Difference of Solubility

As described above, in the process of preparing a 3M $MASnI_3$ precursor solution, Comparative Example 1 using the sublimation purified $SnI_2$ took one hour to completely dissolve it, meanwhile Examples 3 and 4 respectively using $SnI_2 \cdot DMF$ of Example 1 and $3SnI_2 \cdot 2DMF$ of Example 2 took only about 3 minutes, proving a dramatical improvement in solubility.

Test Example 2: Release Temperature of Solvent Molecule

Figure 13:
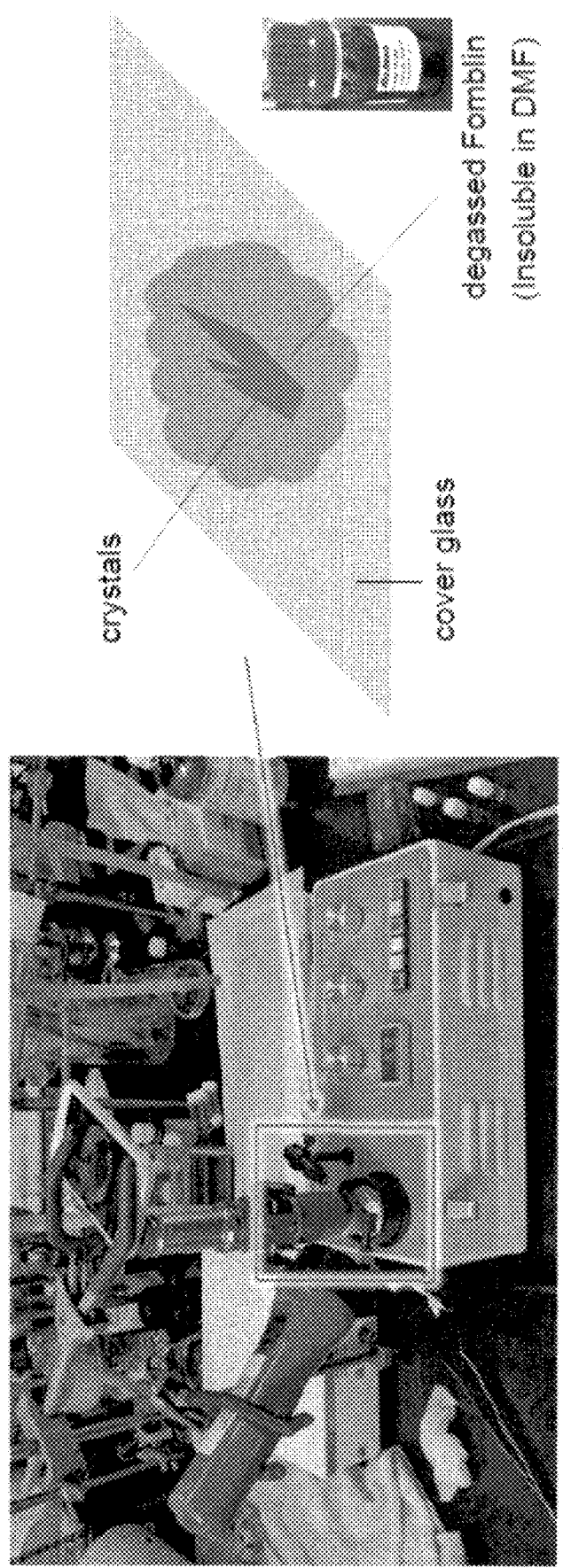
FIG. 13 illustrates a micro melting point apparatus used in Test Example 2.
Figure 14:
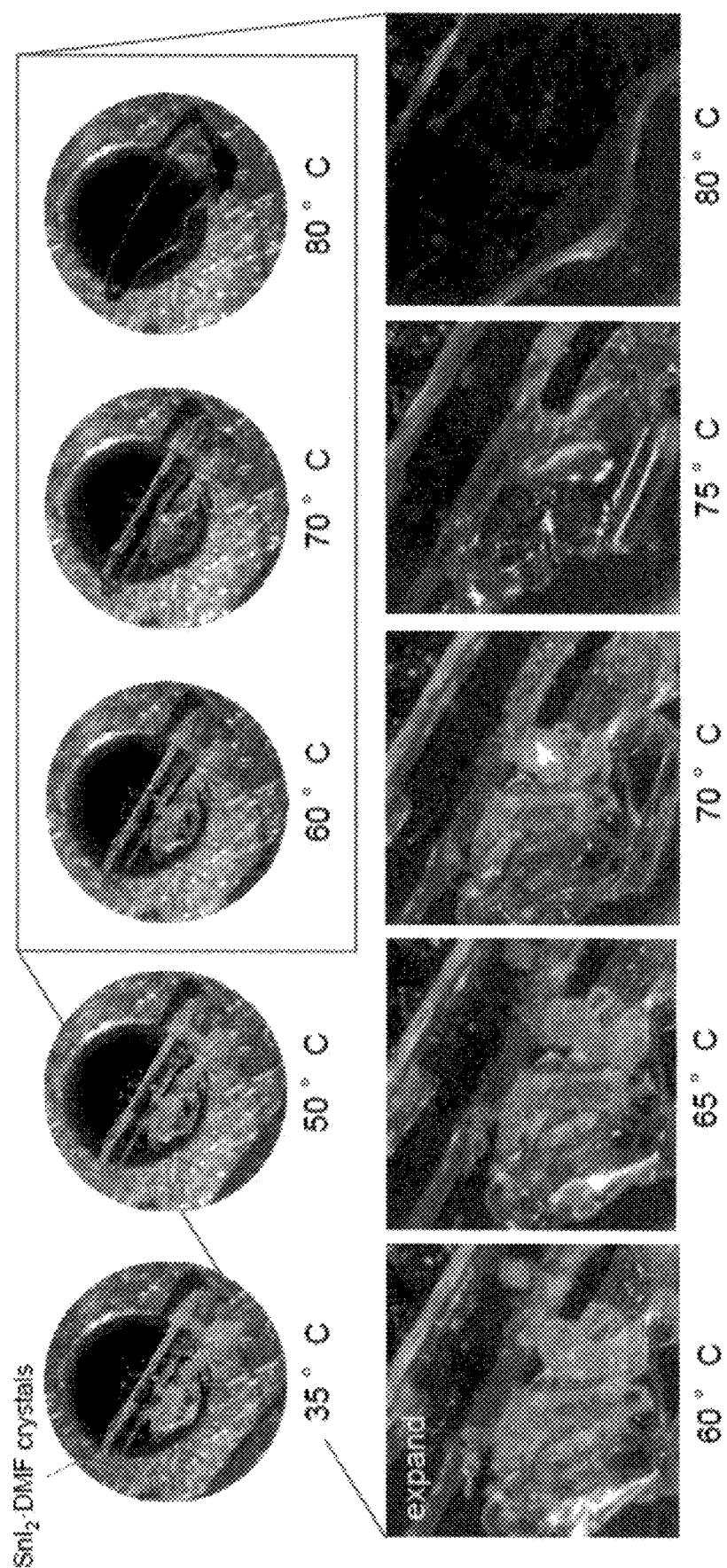
FIG. 14 illustrates results of Test Example 2.

Using a micro melting point apparatus illustrated in FIG. 13, release temperature of DMF was measured under heating, while minimizing an effect of air oxidation by immersing the crystal ($SnI_2 \cdot DMF$) obtained in Example 1 in an oil (deaerated Fomblin (registered trademark)). Results are shown in FIG. 14. From the results, the crystal was found to start melting at around 68.5° C., and rapidly melted at around 75° C. From these facts, it is understood that the crystal when heated releases DMF at around 70° C. to produce $SnI_2$. Note that a crystal ($SnI_2 \cdot DMSO$) in Example 5, described later, can also release DMSO under heating.

Example 5: $SnI_2 \cdot DMSO$

Figure 15:
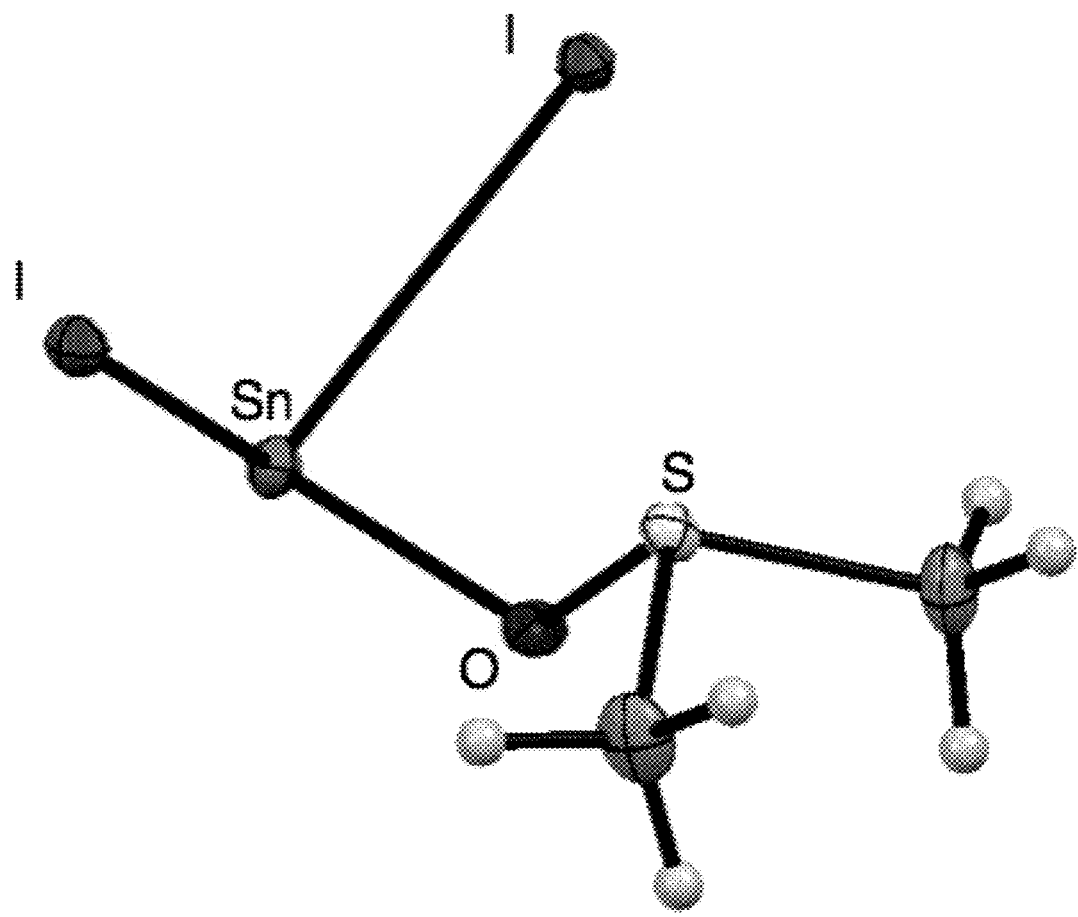
FIG. 15 illustrates a result (ORTEP chart) of single crystal X-ray crystallography of a compound ($SnI_2 \cdot DMSO$) obtained in Example 5, showing an $SnI_2$ molecule on the left, and a DMSO molecule on the right.
Figure 16:
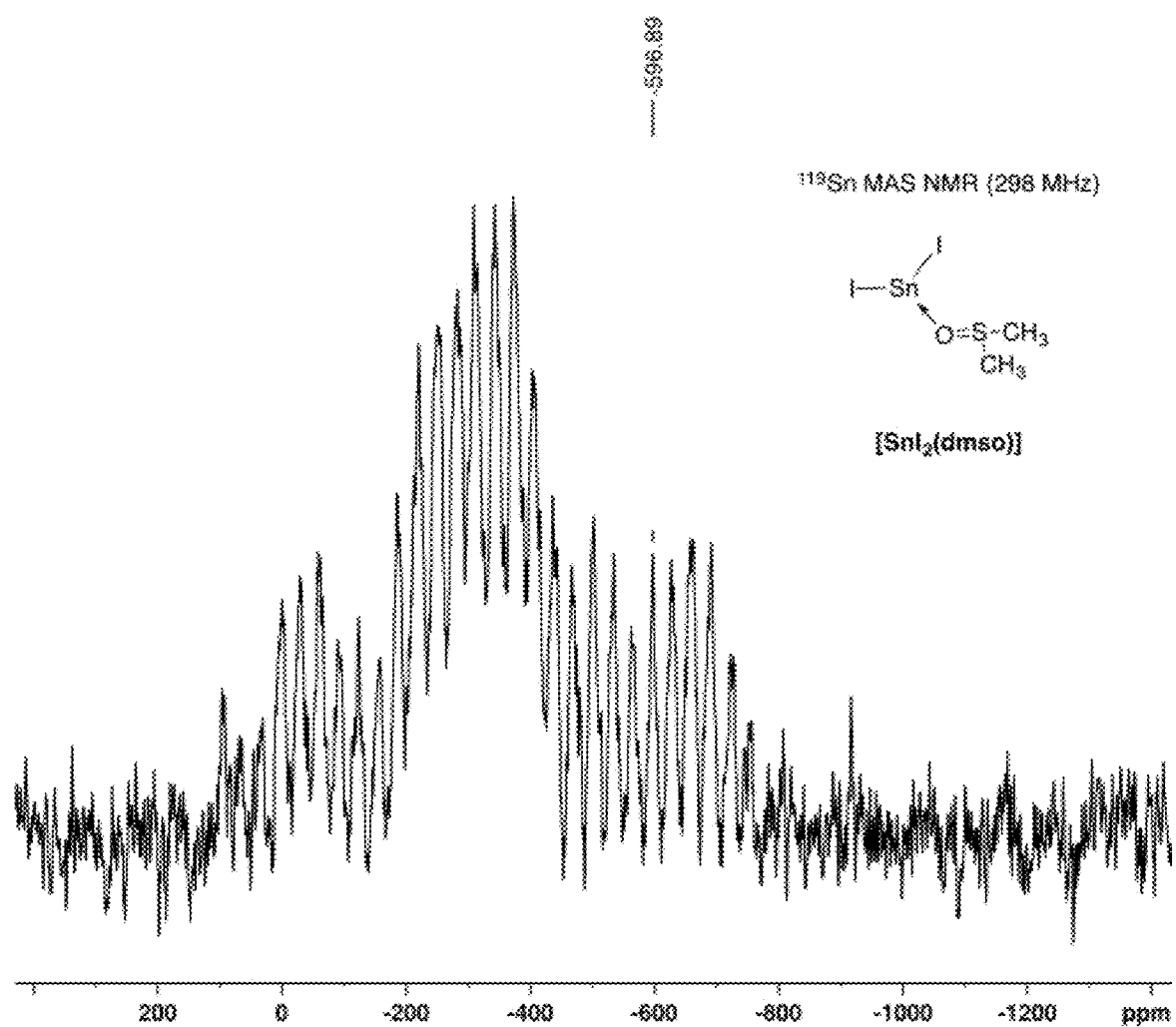
FIG. 16 is a $^{119}$Sn MAS NMR spectrogram of the compound ($SnI_2 \cdot DMSO$) obtained in Example 5.

In a globe box, $SnI_2$ (429 mg, 1.2 mmol; sublimation purified product, from Tokyo Chemical Industry Co., Ltd.) was allowed to dissolve into super dehydrated DMSO (576 µL; from Wako Pure Chemical Company). After being stirred at 55° C. for two hours, the content was filtered through a PTFE filter. The filtrate was then transferred into a test tube with a screw cap, approximately 10 mL of methylene chloride as a poor solubility solvent was slowly poured, and the content was allowed to recrystallize by the double layer diffusion method. Two days after, $SnI_2 \cdot DMSO$ was obtained as a colorless needle crystal. Yield was 45% (235 mg, 0.5 mmol). Obtained single crystal was analyzed by single crystal X-ray crystallography, to clarify the detailed structure (FIG. 15). FIG. 16 is a $^{119}Sn$ MAS NMR spectrogram of a compound ($SnI_2 \cdot DMSO$) obtained in Example 5.

mp: 75.0° C.; Crystal data: $C_2H_6I_2OSSn$; FW=450.62, crystal size 0.18×0.08×0.05 mm, Monoclinic, $P2_1/c$, a=4.4931(7) Å, b=16.364(3) Å, c=12.2211(19) Å, ƒβ=94.7866(18°), V=1282.0(9) Å$^3$, Z=4, $D_c$=3.343 g/cm$^3$. The refinement converged to $R_1$=0.0183, $wR_2$=0.0344 (I>2σ(I)), GOF=0.974.

Example 6: $SnBr_2 \cdot 2DMSO$

Figure 17:
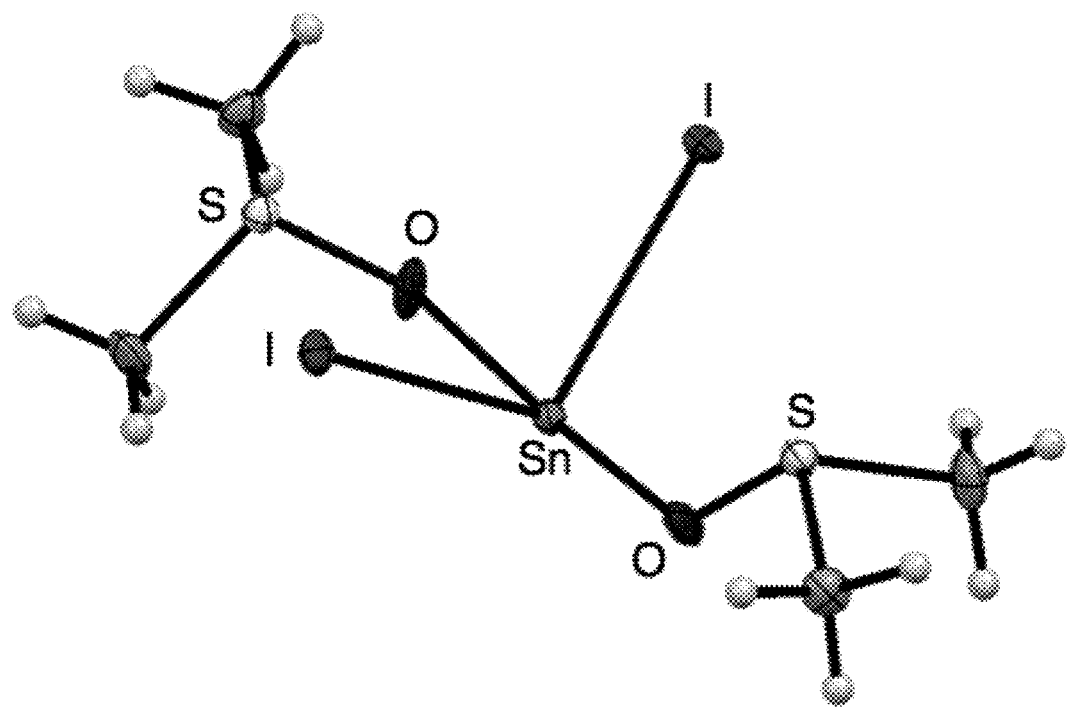
FIG. 17 illustrates a result (ORTEP chart) of single crystal X-ray crystallography of a compound ($SnBr_2 \cdot 2DMSO$) obtained in Example 6, showing an $SnBr_2$ molecule at the center, and DMSO molecules on the left and right ends.
Figure 18:
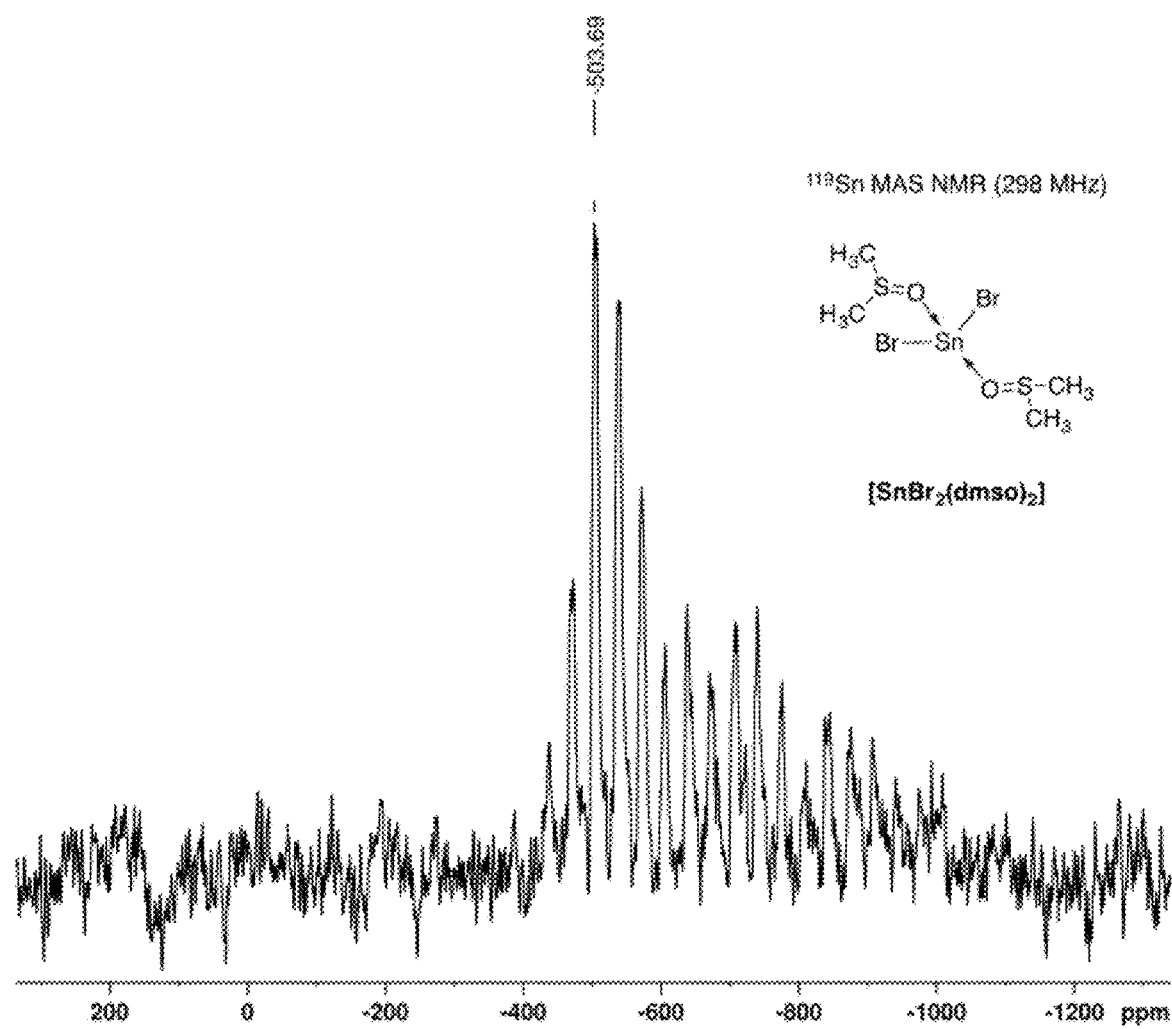
FIG. 18 is a $^{119}$Sn MAS NMR spectrogram of the compound ($SnBr_2 \cdot 2DMSO$) obtained in Example 6.

In a globe box, $SnBr_2$ (2.0 g, 7.2 mmol; from Aldrich) was allowed to dissolve into super dehydrated DMSO (1.8 mL;

from Wako Pure Chemical Company). After being stirred at 55° C. for two hours, the content was filtered through a PTFE filter. The filtrate was then transferred into a test tube with a screw cap, approximately 10 mL of methylene chloride as a poor solubility solvent was slowly poured, and the content was allowed to recrystallize by the double layer diffusion method. Two days after, $SnBr_2 \cdot 2DMSO$ was obtained as a colorless needle crystal. Yield was 70% (2.2 g, 5.1 mmol). Obtained single crystal was analyzed by single crystal X-ray crystallography, to clarify the detailed structure (FIG. 17). FIG. 18 is a $^{119}Sn$ MAS NMR spectrogram of a compound ($SnBr_2 \cdot 2DMSO$) obtained in Example 6.

Crystal data: $C_4H_{12}Br_2O_2S_2Sn$; FW=433.42, crystal size 0.10×0.04×0.04 mm, Orthorhombic, $Aba_2$, a=10.666(2) Å, b=13.535(3) Å, c=8.1116(17) Å, V=1171.0(14) Å$^3$, Z=4, $D_c$=2.969 g/cm$^3$. The refinement converged to $R_1$=0.0152, $wR_2$=0.0312 (I>2σ(I)), GOF=0.860.

Example 7: $SnF_2$; DMSO

Figure 19:
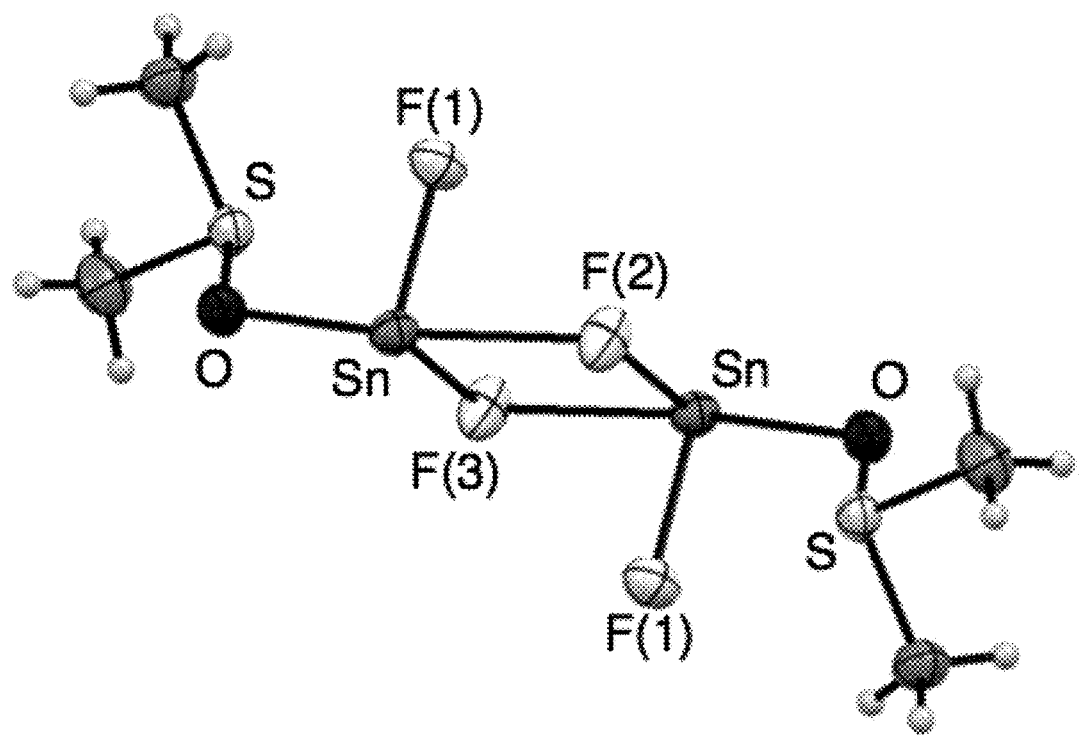
FIG. 19 illustrates a result (ORTEP chart) of single crystal X-ray crystallography of a compound ($SnF_2 \cdot DMSO$) obtained in Example 7, showing an $SnF_2$ molecule on the top, and a DMSO molecule on the bottom.
Figure 20:
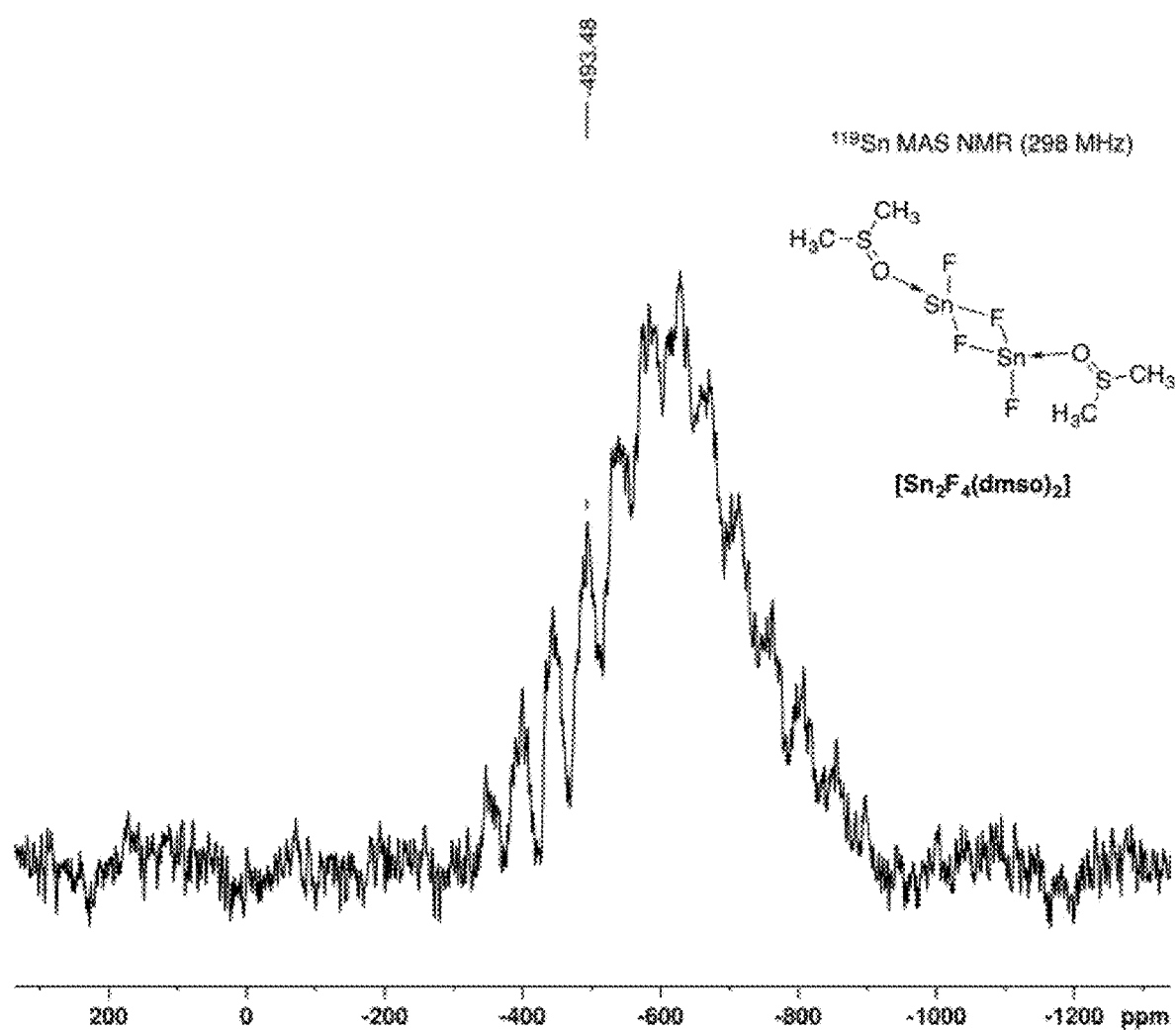
FIG. 20 is a $^{119}$Sn MAS NMR spectrogram of the compound ($SnF_2 \cdot DMSO$) obtained in Example 7.

In a globe box, $SnF_2$ (940 mg, 6.0 mmol; from Aldrich) was allowed to dissolve into super dehydrated DMSO (2.0 mL; from Wako Pure Chemical Company). After being stirred at 50° C. for 30 minutes, the content was filtered through a PTFE filter. The filtrate was then transferred into a test tube with a screw cap, approximately 10 mL of methylene chloride as a poor solubility solvent was slowly poured, and the content was allowed to recrystallize by the double layer diffusion method. One day after, $SnF_2 \cdot DMSO$ was obtained as a colorless needle crystal. Yield was 26% (368 mg, 1.6 mmol). Obtained single crystal was analyzed by single crystal X-ray crystallography, to clarify the detailed structure (FIG. 19). FIG. 20 is a $^{119}Sn$ MAS NMR spectrogram of a compound ($SnF_2 \cdot DMSO$) obtained in Example 7.

Crystal data: $C_2H_6F_2OSSn$; FW=234.82, crystal size 0.13×0.11×0.08 mm, Triclinic, P-1, a=5.7373(19) Å, b=7.827(3) Å, c=7.981(3) Å, V=318.69(18) Å$^3$, Z=1, $D_c$=2.694 g/cm$^3$. The refinement converged to $R_1$=0.0144, $wR_2$=0.0368 (I>2σ(I)), GOF=1.168.

Example 8: $Bi(DMF)_8 \cdot Bi_3I_{12}$

In a globe box, $BiI_3$ (1769 mg, 3.0 mmol; from Aldrich) was allowed to dissolve into super dehydrated DMF (1.5 mL; from Wako Pure Chemical Company). After being stirred at 50° C. for one hour, the content was filtered through a PTFE filter. The filtrate was then transferred into a test tube with a screw cap, approximately 10 mL of methylene chloride as a poor solubility solvent was slowly poured, and the content was allowed to recrystallize. One day after, $Bi(DMF)_8 \cdot Bi_3I_{12}$ was obtained as a red crystal. Yield was 84% (1852 mg, 0.6 mmol). Obtained single crystal was analyzed by single crystal X-ray crystallography, to clarify the detailed structure.

Crystal data: $C_{24}H_{56}N_8O_8I_{12}Bi_4$; FW=2943.12, crystal size 0.12×0.10×0.06 mm, Monoclinic, $P2_1/c$, a=15.1041(12) Å, b=30.885(3) Å, c=15.7523(13) Å, V=6505.0(9) Å$^3$, Z=33, $D_c$=5.330 g/cm$^3$. The refinement converged to $R_1$=0.0349, $wR_2$=0.0776 (I>2σ(I)), GOF=1.088.

Example 9: $Bi(DMSO)_8 \cdot Bi_2I_9$

In a globe box, $BiI_3$ (590 mg, 1.0 mmol; from Aldrich) was allowed to dissolve into super dehydrated DMSO (0.5 mL; from Wako Pure Chemical Company). After being stirred at 60° C. for 30 minutes, the content was filtered through a PTFE filter. The filtrate was then transferred into a test tube with a screw cap, approximately 3 mL of methylene chloride as a poor solubility solvent was slowly poured, and the content was allowed to recrystallize. One day after, $Bi(DMSO)_8 \cdot Bi_2I_9$ was obtained as a red crystal. Yield was 78% (625 mg, 0.3 mmol). Obtained single crystal was analyzed by single crystal X-ray crystallography, to clarify the detailed structure.

Crystal data: $C_{16}H_{48}O_8S_8I_9Bi_3$; FW=2377.9, crystal size 0.11×0.10×0.05 mm, Triclinic, P-1, a=12.3313(10) Å, b=14.8247(12) Å, c=16.2663(13) Å, V=2727.0(4) Å$^3$, Z=2, $D_c$=2.919 g/cm$^3$. The refinement converged to $R_1$=0.0284, $wR_2$=0.0595 (I>2σ(I)), GOF=1.018.

Example 10: $SnBr_2 \cdot DMF$

Figure 21:
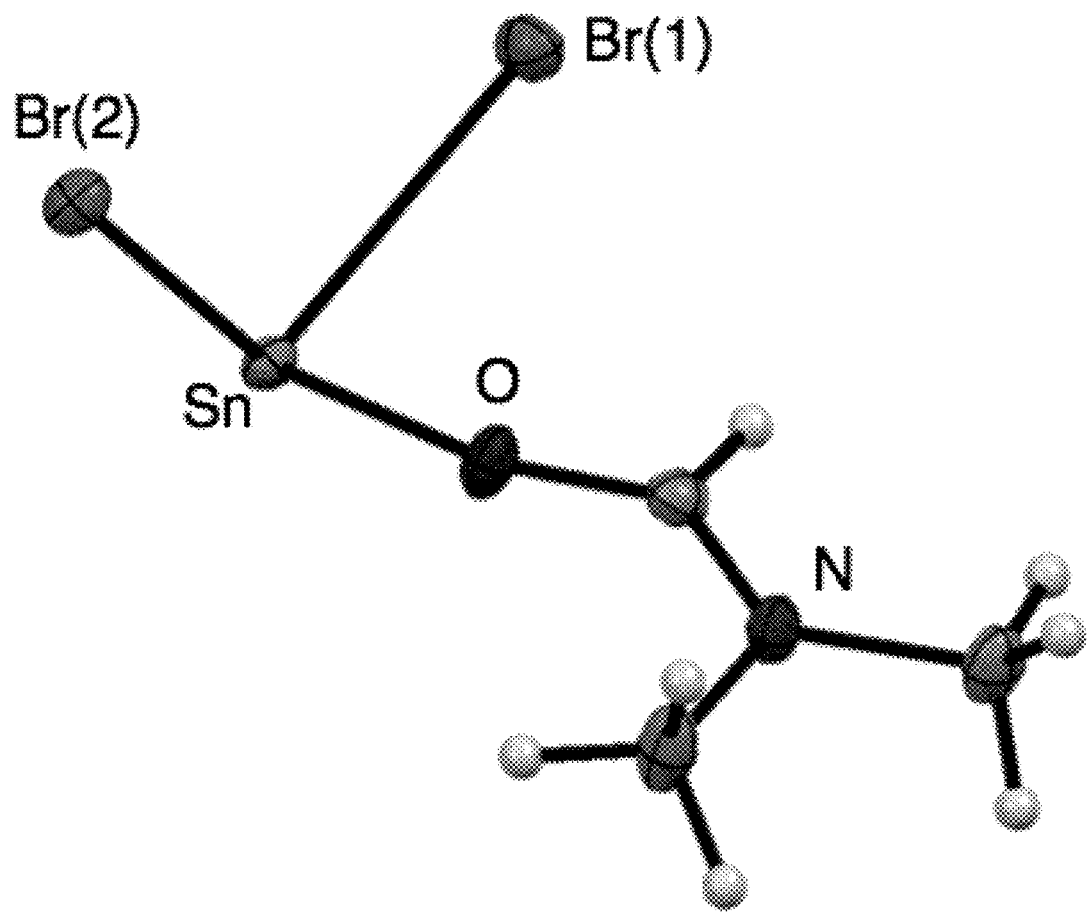
FIG. 21 illustrates a result (ORTEP chart) of single crystal X-ray crystallography of a compound ($SnBr_2.DMF$) obtained in Example 10, showing an $SnBr_2$ molecule on the left, and a DMF molecule on the right.

In a globe box, $SnBr_2$ (1.67 g, 6.0 mmol; from Aldrich)) was allowed to dissolve into super dehydrated DMF (1.5 mL; from Wako Pure Chemical Company). After being stirred at 50° C. for 30 minutes, the content was filtered through a PTFE filter. The filtrate was then transferred into a test tube with a screw cap, approximately 15 mL of toluene as a poor solubility solvent was slowly poured, and the content was allowed to recrystallize by the double layer diffusion method. One day after, $SnBr_2 \cdot DMF$ was obtained as a colorless needle crystal. Yield was 28.3% (597 mg, 1.7 mmol). Obtained single crystal was analyzed by single crystal X-ray crystallography, to clarify the detailed structure (FIG. 21).

Crystal data: $C_3H_7Br_2NOSn$; FW=351.61, crystal size 0.14×0.08×0.05 mm, Monoclinic, $P2_1/c$, a=4.3126(11) Å, b=16.772(4) Å, c=11.735(3) Å, β=98.548(3°), V=839.4(4) Å$^3$, Z=4, $D_c$=2.782 g/cm$^3$. The refinement converged to $R_1$=0.0176, $wR_2$=0.0358 (I>2σ(I)), GOF=1.003.

Example 11: $3SnI_2 \cdot 2DMF$

Figure 22:
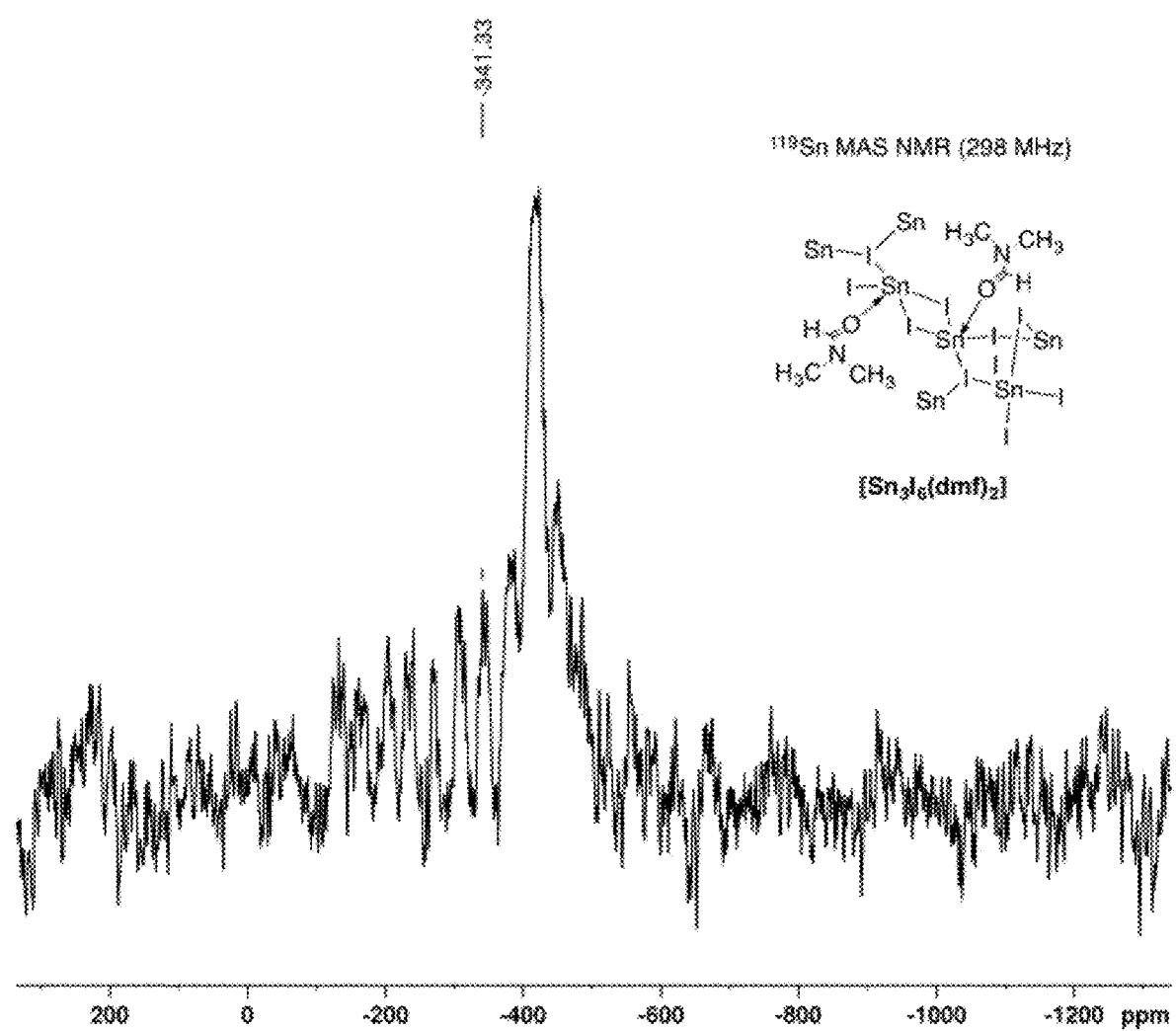
FIG. 22 is a $^{119}$Sn MAS NMR spectrogram of a compound (3SnI$_2$·2DMF) obtained in Example 11.

In a globe box filled with an inert gas (Ar), $SnI_2$ (4.3 g, 11.7 mmol; sublimation purified product) was dissolved into dehydrated and degassed DMF (2.9 ml). The content was stirred at 50° C. for one hour, and the obtained yellow suspension was filtered through a PTFE filter (pore size=0.45 μm), to remove an insoluble matter. Dichloromethane ($CH_2Cl_2$: approx. 15 mL) as a poor solubility solvent was slowly poured. The content was allowed to stand still at room temperature for two days, and then filtered, to obtain 1.2 g (0.9 mmol, yield=30%) of $3SnI_2 \cdot 2DMF$ in the form of orange needle crystal. FIG. 22 is a $^{119}Sn$ MAS NMR spectrogram of a compound ($3SnI_2 \cdot 2DMF$) obtained in Example 11.

$^{119}Sn$ MAS NMR (298 MHz): δ −341.33.

Example 12: $SnI_2 \cdot 2DMSO$

Figure 23:
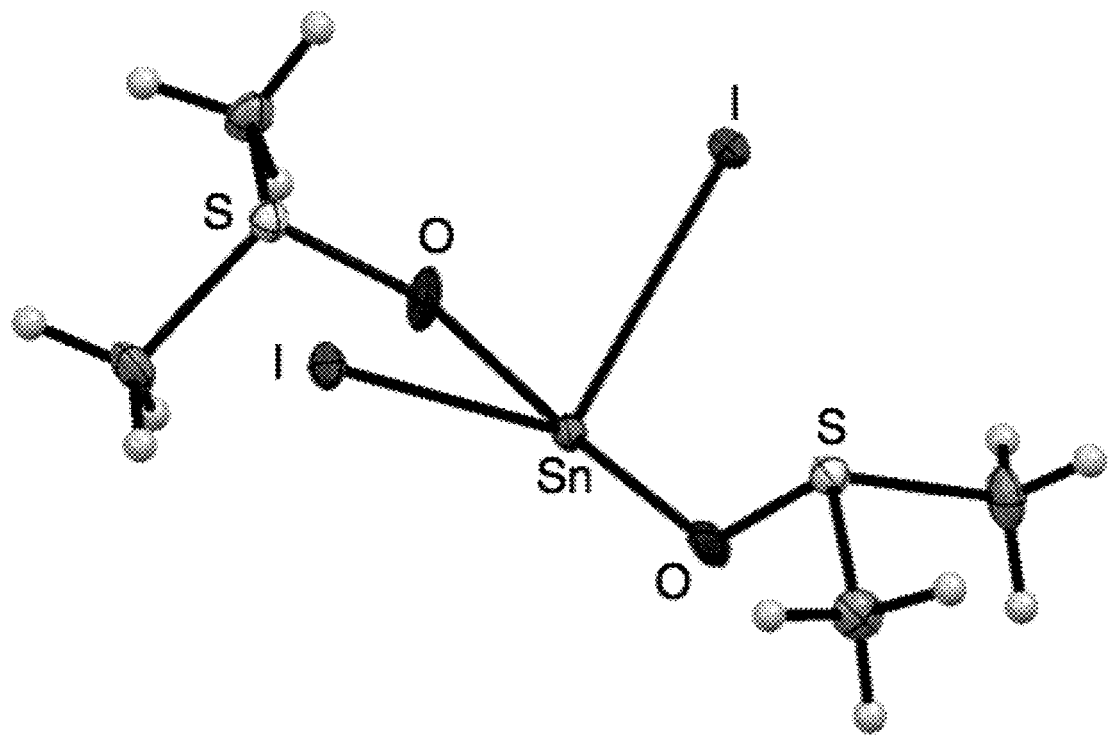
FIG. 23 illustrates a result of single crystal X-ray crystallography of a compound (SnI$_2$·2DMSO) obtained in Example 12.
Figure 24:
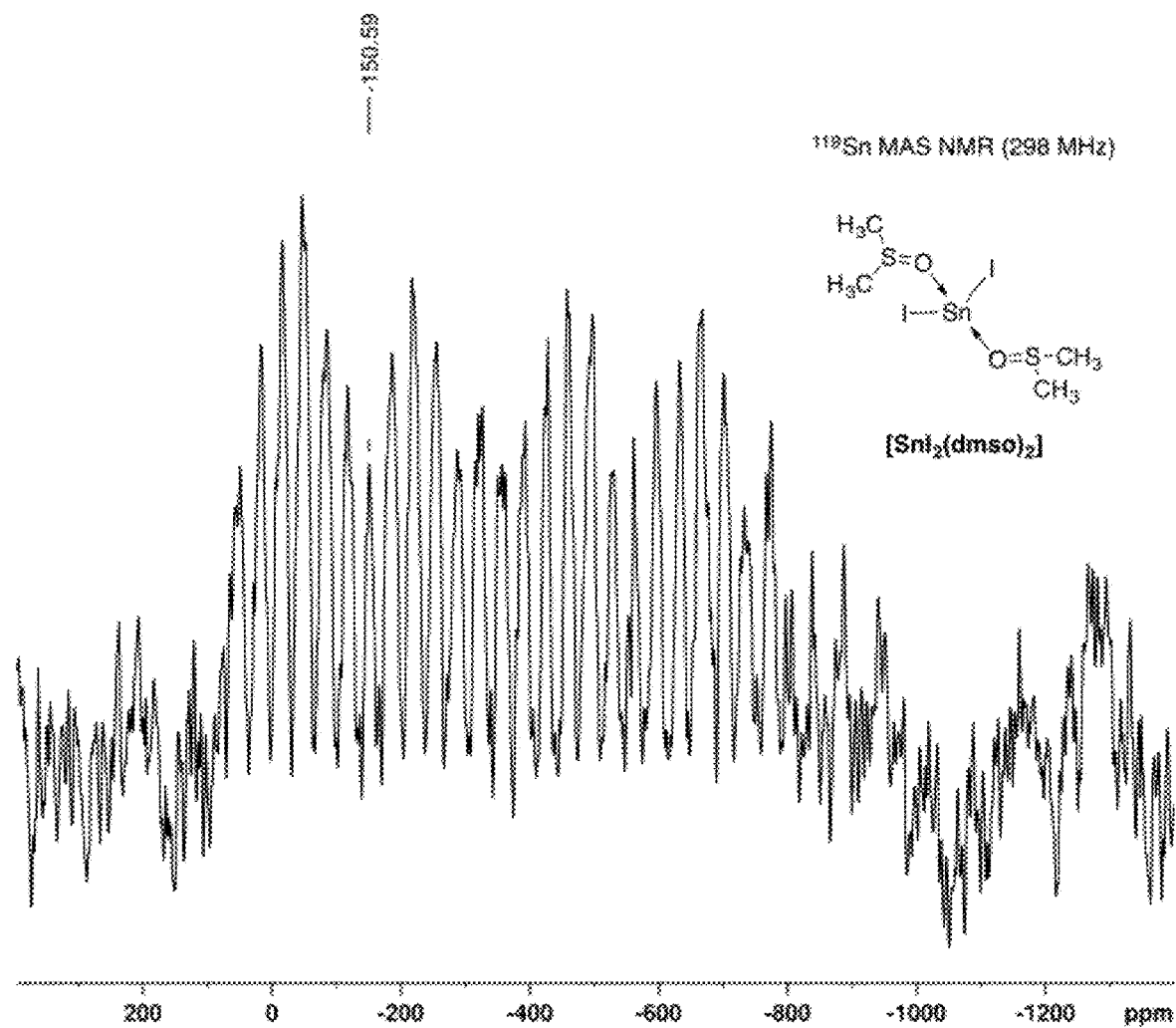
FIG. 24 is a $^{119}$Sn MAS NMR spectrogram of the compound (SnI$_2$·2DMSO) obtained in Example 12.

In a globe box filled with an inert gas (Ar), $SnI_2$ (5015 mg, 13.5 mmol; sublimation purified product) was dissolved into dehydrated and degassed DMSO (8.0 ml). The content was stirred at 90° C. for 30 minutes, and the obtained yellow suspension was filtered through a PTFE filter (pore size=0.45 μm), to remove an insoluble matter. Toluene (approx. 40 mL) as a poor solubility solvent was slowly poured. The content was allowed to stand still at room temperature for one day, and then filtered, to obtain 6194 mg (11.7 mmol, yield=87%) of $SnI_2 \cdot 2DMSO$ in the form of colorless crystal. FIG. 23 illustrates a result of single crystal X-ray crystallography of a compound ($SnI_2 \cdot 2DMSO$) obtained in Example 12. FIG. 24 is a $^{119}Sn$ MAS NMR spectrogram of the compound (SnI$_2$·2DMSO) obtained in Example 12. $^{119}$Sn MAS NMR (298 MHz): δ −150.59. Elemental ratios (%) regarding C$_4$H$_{12}$I$_2$O$_2$S$_2$Sn were as follows: calculated: C, 9.09, H, 2.29, N, 0.00; found: C, 9.18, H, 2.22, N, 0.00.

Example 13: SnBr$_2$·DMF

Figure 25:
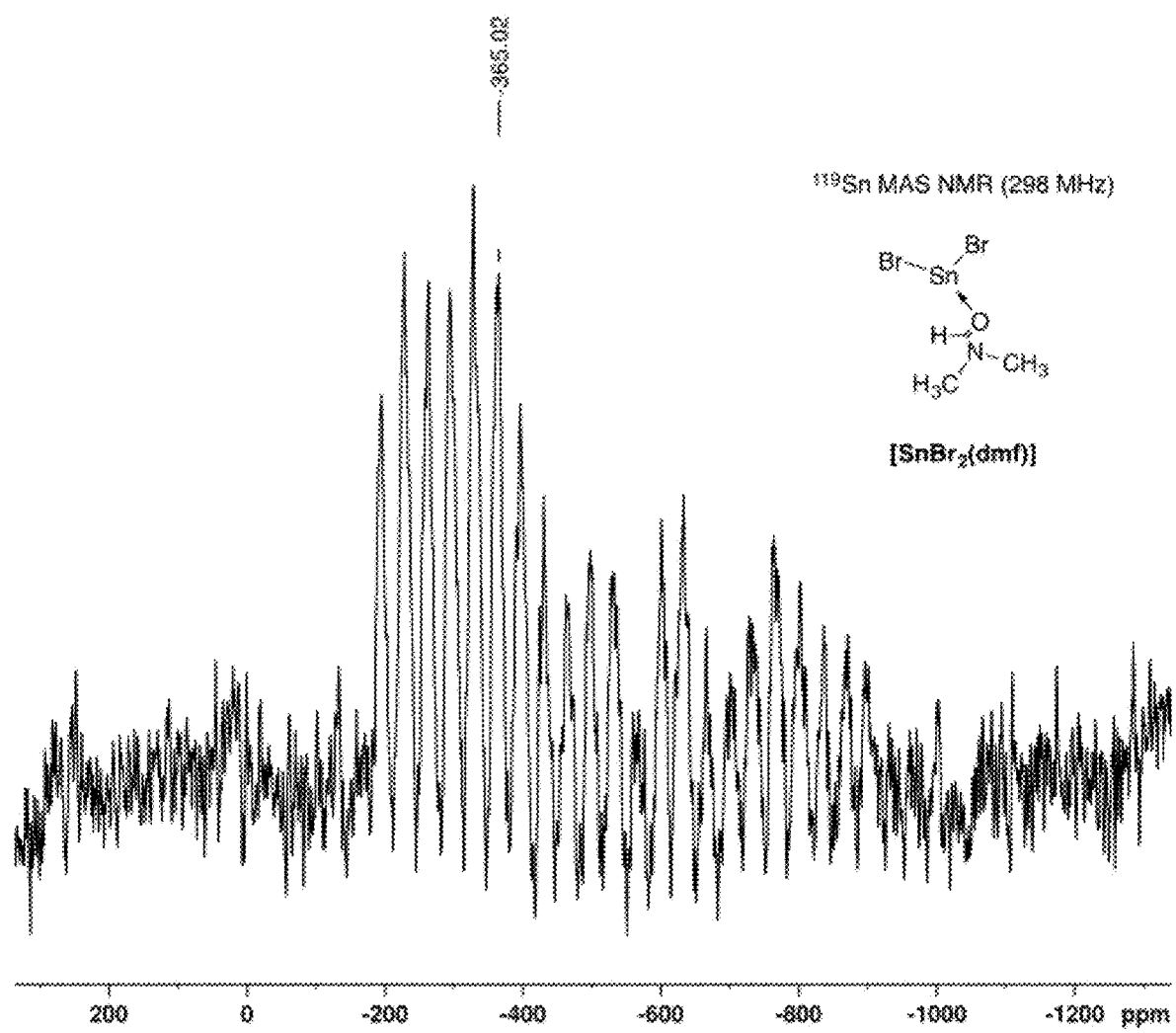
FIG. 25 is a $^{119}$Sn MAS NMR spectrogram of a compound (SnBr$_2$.DMF) obtained in Example 13.

In a globe box filled with an inert gas (Ar), SnBr$_2$ (1670 mg, 6.0 mmol, 99.8%, Br based) was dissolved into dehydrated and degassed DMF (1.5 mL). The content was stirred at 50° C. for 30 minutes, and the obtained colorless solution was filtered through a PTFE filter (pore size=0.45 µm). Toluene (approx. 15 mL) as a poor solubility solvent was slowly poured. The content was allowed to stand still at room temperature for one day, and then filtered, to obtain 597 mg (1.7 mmol, yield=28%) of SnBr$_2$·DMF in the form of colorless crystal. FIG. 25 is a $^{119}$Sn MAS NMR spectrogram of a compound (SnBr$_2$·DMF) obtained in Example 13.

$^{119}$Sn MAS NMR (298 MHz): δ −365.02. Elemental ratios (%) regarding C$_3$H$_7$BR$_2$NOSn were as follows: calculated: C, 10.25, H, 2.01, N, 3.98; found: C, 10.22, H, 1.94, N, 3.98.

Example 14: SnCl$_2$·DMF

Figure 26:
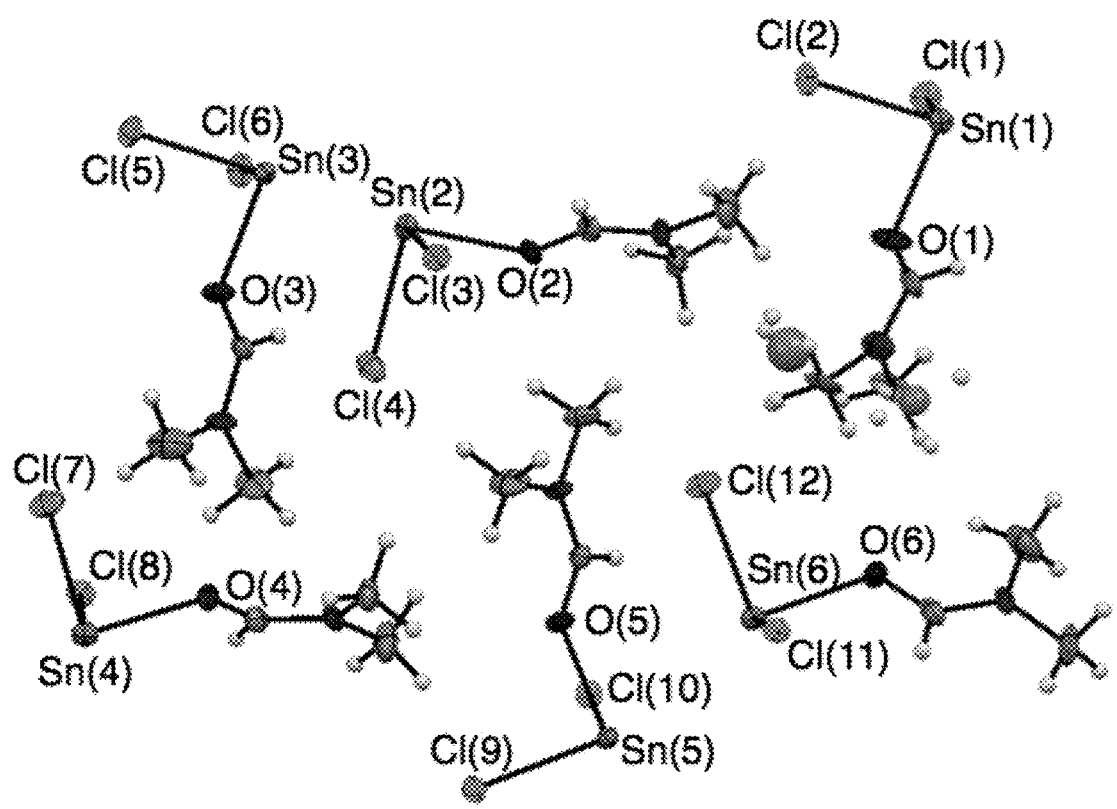
FIG. 26 illustrates a result of single crystal X-ray crystallography of a compound (SnCl$_2$.DMF) obtained in Example 14.
Figure 27:
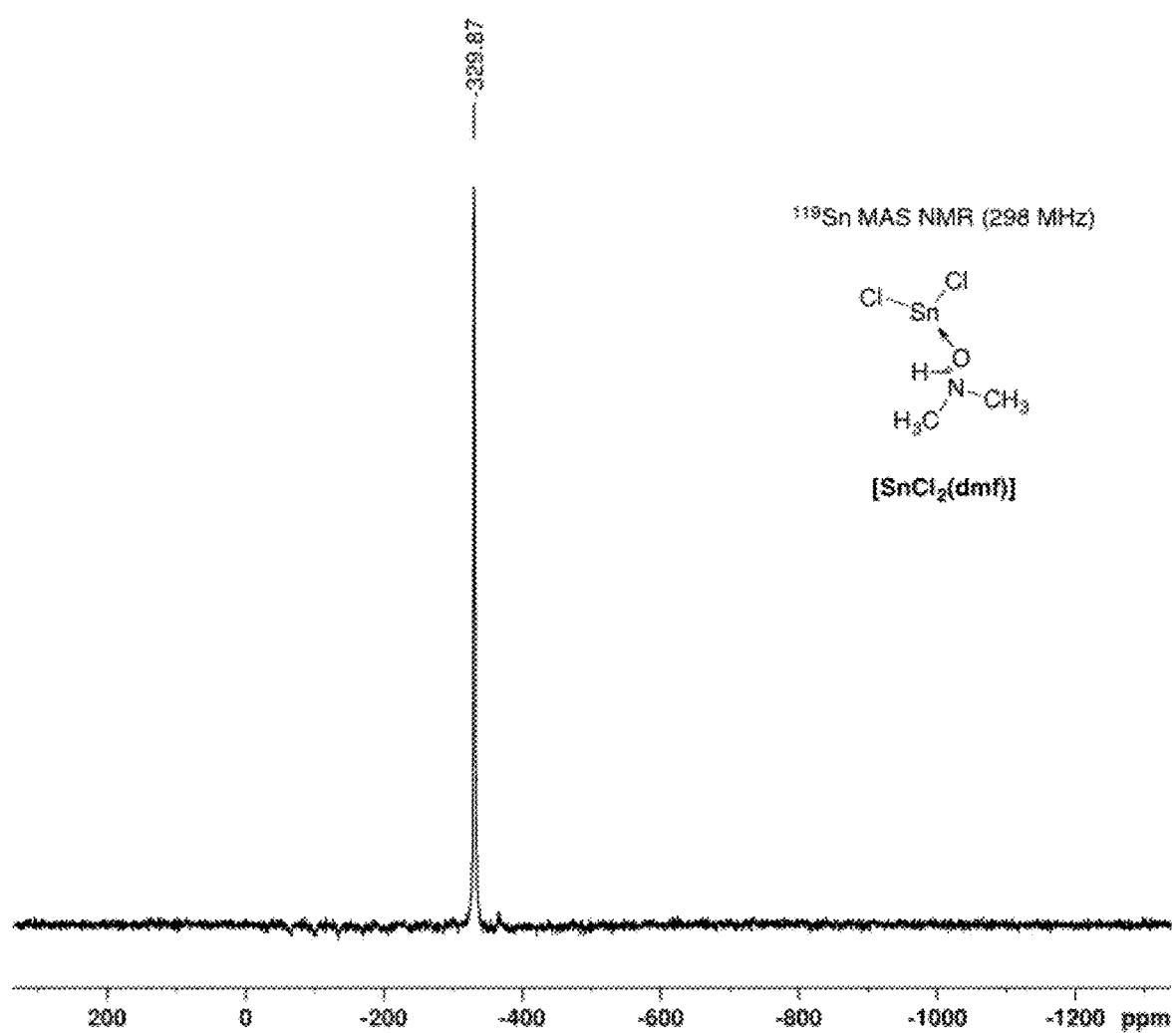
FIG. 27 is a $^{119}$Sn MAS NMR spectrogram of a compound (SnCl$_2$.DMF) obtained in Example 14.

In a globe box filled with an inert gas (Ar), SnCl$_2$ (3.99 g, 21.0 mmol, 97%) was dissolved into dehydrated and degassed DMF (3 mL). The content was stirred at 80° C. for 30 minutes, and the obtained colorless solution was filtered through a PTFE filter. Toluene (approx. 10 mL) as a poor solubility solvent was slowly poured. The content was allowed to stand still at room temperature for one day, and then filtered, to obtain 2.71 g (10.3 mmol, yield=49%) of SnCl$_2$·DMF in the form of colorless needle crystal. FIG. 26 illustrates a result of single crystal X-ray crystallography of a compound (SnCl$_2$·DMF) obtained in Example 14. FIG. 27 is a $^{119}$Sn MAS NMR spectrogram of the compound (SnCl$_2$·DMF) obtained in Example 14.

$^{119}$Sn MAS NMR (298 MHz): δ −329.87.

Elemental ratios (%) regarding C$_3$H$_7$C$_{12}$NOSn were as follows: calculated: C, 13.72, H, 2.69, N, 5.53; found: C, 13.74, H, 2.68, N, 5.35.

Example 15: MASnI$_3$ (Started from SnI$_2$·2DMSO of Example 12)

Preparation of MASnI$_3$ Film Sample

Using SnI$_2$·2DMSO (793.2 mg, 1.5 mmol) in DMSO (1 mL) and methyl ammonium iodide (MAI, 238.5 mg, 1.5 mmol), 1.5 M of MASnI$_3$ was obtained. The mixed powder was allowed to dissolve at 25° C. over a period of 30 minutes, and the content was filtered through a PTFE filter (pore size=0.45 µm). The obtained filtrate (200 µL) was spin coated over a washed glass substrate at 5000 rpm for 7 seconds. Using 450 µL of toluene, dropwise addition of poor solubility solvent was carried out 3 seconds before the end of spin coating. The substrate was then annealed on a hot plate at 35° C. for 5 minutes, at 45° C. for 5 minutes, and at 70° C. for 20 minutes. After the annealing, a 50 mg/mL PMMA solution in chlorobenzene (PhCl) was spin coated over the MASnI$_3$ film at 1500 rpm for 45 seconds.

Example 16: FASnI$_3$ (Started from SnI$_2$·2DMSO of Example 12)

Preparation of FASnI$_3$ Film Sample

Using SnI$_2$·2DMSO (793.2 mg, 1.5 mmol) and formamidinium iodide (FAI, 258.0 mg, 1.5 mmol) (1:1 molar ratio), 1.5 M of FASnI$_3$ was obtained. These powders were allowed to dissolve at 25° C. over a period of 30 minutes into a 3:1 (v/v) mixed solvent of DMF (0.75 mL) and DMSO (0.25 mL). The filtrate was filtered through a PTFE filter (pore size=0.45 µm). Thereafter, 200 µL of filtrate was spin coated over a washed glass substrate at 4000 rpm for 60 seconds. Using 450 µL of toluene, dropwise addition of poor solubility solvent was carried out 5 seconds before the end of spin coating. The substrate was then annealed on a hot plate at 35° C. for 5 minutes, at 45° C. for 5 minutes, and at 70° C. for 20 minutes. After the annealing, a 50 mg/mL PMMA solution in PhCl was spin coated over the FASnI$_3$ film at 1500 rpm for 45 seconds.

Example 17: FASnI$_3$ (Started from SnI$_2$·2DMSO of Example 12 and SnI$_2$ just as Sublimation Purified)

Preparation of FASnI$_3$ Film Sample Associated with 10 mol % of SnF$_2$ According to a method similar to that for preparing the FASnI$_3$ film, powders (1:1 molar ratio) of SnI$_2$·2DMSO (793.2 mg, 1.5 mmol) and formamidinium iodide (FAI, 258.0 mg, 1.5 mmol, TCI), used as a starting material, and SnF$_2$ (23.5 mg, 0.15 mmol) were dissolved into a 3:1 (v/v) mixed solvent of DMF (0.75 mL) and DMSO (0.25 mL) at 25° C. After filtration through a 0.45 µm filter, the obtained filtrate (200 µL) was spin coated over a washed glass substrate at 4000 rpm for 60 seconds. Using 450 µL of toluene, dropwise addition of poor solubility solvent was carried out 5 seconds before the end of spin coating. The substrate was then annealed on a hot plate at 35° C. for 5 minutes, at 45° C. for 5 minutes, and at 70° C. for 20 minutes. After the annealing, a 50 mg/mL PMMA solution in PhCl was spin coated over the FASnI$_3$ film at 1500 rpm for 45 seconds.

Example 18: Preparation of MASnI$_3$ Crystal Sample

SnI$_2$·DMF (445 mg, 1.00 mmol) and MAI (158 mg, 1.00 mmol) were dissolved in ethanol (3 mL), and the reaction mixture was stirred at 80° C. for 30 minutes. The pale green solution was cooled to obtain a blackish green crystalline powder (355 mg, 0.667 mmol, 67%). The crystalline powder was collected by filtration, washed with ethanol, and dried in vacuo.

Example 19: Preparation of FASnI$_3$ Crystal Sample

Preparation of FASnI$_3$ Crystal Sample

By a method similar to that for MASnI$_3$, 133 mg (0.244 mmol, 61%) of FASnI$_3$ crystalline powder was obtained from a solution prepared by dissolving SnI$_2$·DMF (176 mg, 0.395 mmol) and FAI (65.4 mg, 0.380 mmol) into ethanol (1.5 mL).

Figure 28:
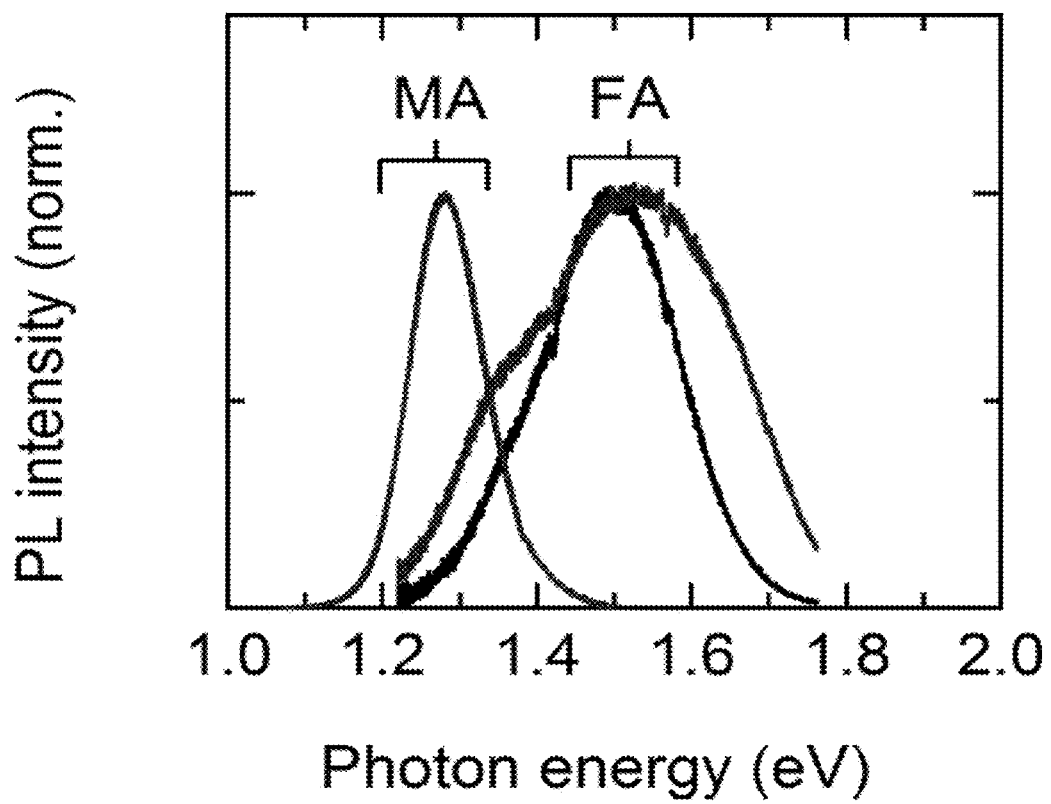
FIG. 28 is a graph, in lieu of drawing, showing photoluminescence (PL) spectra of MASnI$_3$ and FASnI$_3$ obtained without using SnF$_2$, before (dark solid line) and after (pale solid line) atmospheric exposure (approx. 15 minutes), with PL intensity plotted on the ordinate, and photon energy on the abscissa (eV).

Photoluminescence (PL) spectra of MASnI$_3$ and FASnI$_3$ obtained without using SnF$_2$, before (dark solid line) and after (pale solid line) atmospheric exposure (approx. 15 minutes) are shown in FIG. 28. During the atmospheric exposure, absorption was measured in the atmosphere. The film sample of MASnI$_3$ showed no change in the spectral pattern. In contrast, the spectrum of the film of FASnI$_3$ showed large broadening after the atmospheric exposure, indicating that the FASnI$_3$ film sample degraded due to air oxidation, regardless of the surface protection with PMMA. In order to avoid a degrading effect on photophysical properties, a FASnI$_3$ film was prepared by adding 10% SnF$_2$ (well known to improve stability of the sample). From the X-ray diffractometry, the FASnI$_3$ film with an addition of 10% of SnF$_2$ was confirmed to give an XRD pattern identical to the XRD pattern of the FASnI$_3$ film.

Example 20 Manufacture of Perovskite Solar Cell

A glass substrate (25 mm×24 mm, from Geomatec Co., Ltd.) with etched ITO was washed with a neutral detergent and a melamine sponge, and then washed in acetone and IPA in this order for 15 minutes each under ultrasonic wave. After the washing, IPA was blown off using an air gun, followed by UV-ozone cleaning for 15 minutes. Next, poly (3,4-ethylene dioxythiophene) doped with poly (4-styrenesulfonic acid) (PEDOT/PSS) was spin-coated as a hole transport material. The spin coating was designed to perform sloping for one second, spinning at 1000 rpm for 10 seconds, sloping for one second, spinning at 4000 rpm for 60 seconds, and sloping for one second in this order. The obtained film was annealed at 140° C. for 20 minutes.

A mixed solution of 0.9 MFA$_{0.75}$MA$_{0.25}$SnI$_3$ in DMSO solvent and 10 mol % SnF$_2$ was spin-coated. The spin coating was designed to include sloping for 5 seconds, spinning at 5000 rpm for 60 seconds, and sloping for one second. In the last two second period at the maximum speed, 300 μL of chlorobenzene (Ph-Cl) at 65° C. was dropped onto the rotating substrate slowly over one second. The obtained film was annealed at 45° C. for 10 minutes, at 65° C. for 10 minutes or longer, and then at 100° C. for 10 minutes, to manufacture the perovskite layer.

Fullerene C$_{60}$ and BCP (bathocuproin), as the electron transport materials, were stacked over the perovskite layer, by vapor deposition. Lastly, a silver electrode of 100 nm thick was deposited by vacuum deposition, to obtain the perovskite solar cell.

Figure 29:
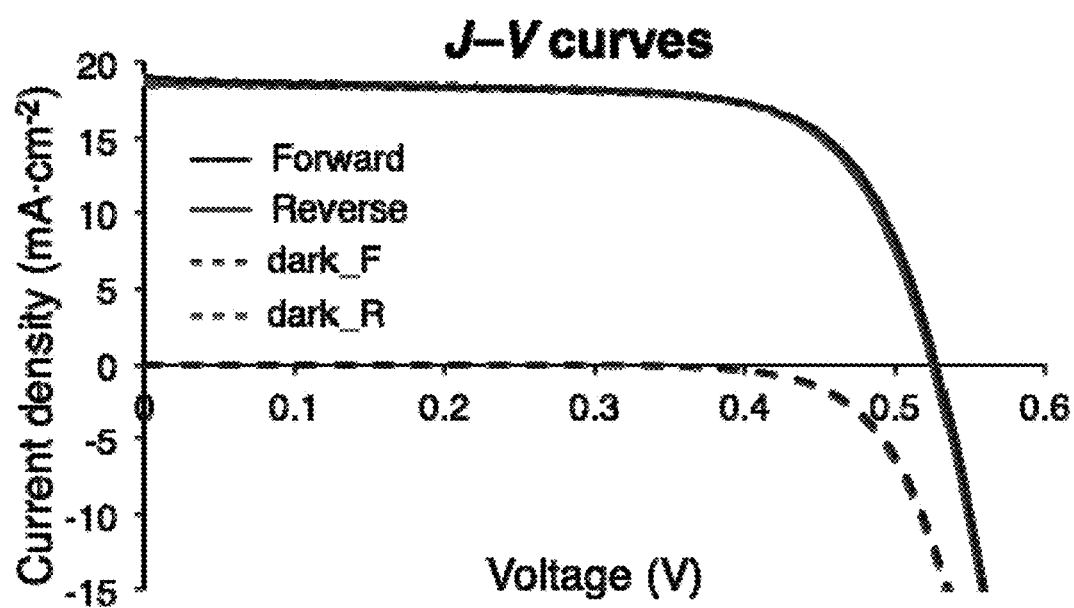
FIG. 29 is a graph, in lieu of drawing, illustrating current density-voltage characteristics of a perovskite solar cell.

The obtained perovskite solar cell was measured regarding current density-voltage characteristics. Results are shown in FIG. 29. FIG. 29 is a graph, in lieu of drawing, illustrating current density-voltage characteristics of the perovskite solar cell obtained in Example. The characteristics are also summarized in Table 1. As shown in Table 1 and FIG. 20, the followings were found: short circuit current density J$_{SC}$=19.05 (18.69) mA cm$^{-2}$, open circuit voltage V$_{OC}$=0.53 (0.52) V, fill factor FF=0.71 (0.72). The photoelectric conversion efficiency (PCE) was found to be 7.09 (7.04)%.

TABLE 1

| J$_{sc}$ (mA·cm$^{-2}$) | V$_{oc}$ (V) | FF | PCE (%) | Rs (Ω·cm$^2$) | Rsh (Ω·cm$^2$) |
|---|---|---|---|---|---|
| 19.05 | 0.53 | 0.71 | 7.09 | 2.6 | 153 |
| 18.69 | 0.52 | 0.72 | 7.04 | 3.0 | 1497 |

Figure 30:
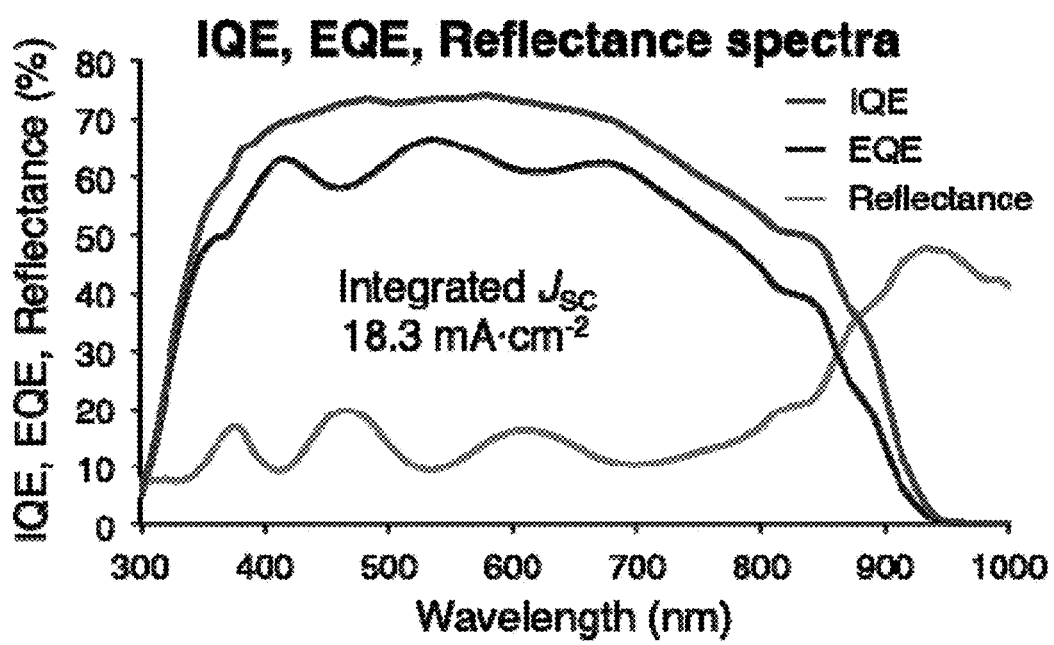
FIG. 30 is a photograph, in lieu of drawing, illustrating reflectance, EQE and IQE spectra.

Also, action spectrum (EQE spectrum) of the obtained perovskite solar cell was measured. FIG. 30 is a photograph, in lieu of drawing, illustrating reflectance, EQE and IQE spectra. The short circuit current density (J$_{SC}$) determined from the EQE spectrum was found to be 18.3 mA·cm$^{-2}$, teaching that the cell can function as a solar cell.

Figure 31:
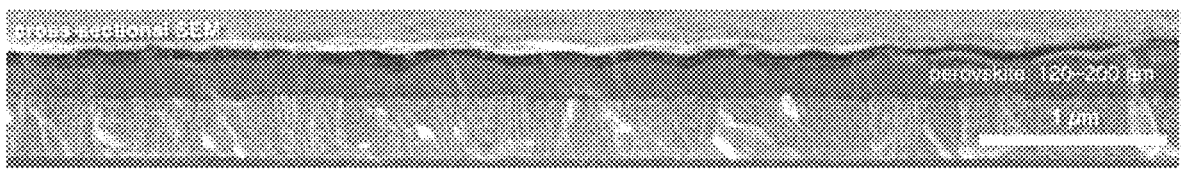
FIG. 31 is an SEM image, in lieu of drawing, of a perovskite solar cell.

The obtained perovskite solar cell was photographed under a SEM. An obtained SEM image is shown in FIG. 31. As seen in FIG. 31, the perovskite solar cell obtained in Example was found to have the individual layers stacked over the substrate. More specifically, over the ITO substrate, formed were the PEDOT/PSS hole transport layer of 20 nm thick, the perovskite layer of 120 to 200 nm thick, the electron transport layer composed of 50 nm thick fullerene (C$_{60}$)/8 nm thick BCP, and the Ag electrode of 100 nm thick.

What is claimed is:

1. An isolated complex represented by formula (1A):

SnX$_n$.(m)L     (1A)

wherein X is an iodine atom or bromine atom, L is N,N-dimethylformamide, n is a value from 1.5 to 2.5, and m is a value from 0.3 to 1.9.

2. The isolated complex according to claim 1, wherein X is an iodine atom.

3. The isolated complex according to claim 1, wherein the complex is a needle crystal.

4. The isolated complex according to claim 1, wherein the complex is a perovskite precursor.

5. The isolated complex according to claim 2, wherein the complex is a perovskite precursor.

6. The isolated complex according to claim 2, wherein the complex is a needle crystal.

* * * * *